US006214548B1

(12) United States Patent
Relman et al.

(10) Patent No.: US 6,214,548 B1
(45) Date of Patent: Apr. 10, 2001

(54) DIAGNOSTIC METHODS FOR CYCLOSPORA

(75) Inventors: David A. Relman, Palo Alto, CA (US); Peter Echeverria, APO AP 96546

(73) Assignees: The United States of America as represented by the Secretary of the Army, Washington, DC (US); Board of Trustees of Leland Stanford Jr. Univ.

(*) Notice: Subject to any disclaimer, the term of this patent is extended or adjusted under 35 U.S.C. 154(b) by 0 days.

(21) Appl. No.: 09/015,259

(22) Filed: Jan. 29, 1998

Related U.S. Application Data
(60) Provisional application No. 60/036,564, filed on Jan. 29, 1997.

(51) Int. Cl.[7] ............... C12Q 1/68; C12P 19/34; C07H 21/02; C07H 21/04; C12N 15/00

(52) U.S. Cl. ............... 435/6; 435/91.2; 536/23.1; 536/24.3; 935/76; 935/77; 935/78

(58) Field of Search ............... 435/6, 91.2; 536/23.1, 536/24.3, 24.32, 24.33; 935/76, 77, 78

(56) References Cited

U.S. PATENT DOCUMENTS

| 5,449,768 | 9/1995 | Chakraborty et al. |
| 5,563,256 | * 10/1996 | Chakraborty et al. ............ 536/24.32 |
| 5,728,526 | * 3/1998 | George et al. ............ 435/6 |
| 5,888,736 | * 3/1999 | Lacroix et al. ............ 435/6 |

FOREIGN PATENT DOCUMENTS

| 516385 A1 | * of 1992 | (EP). |
| WO 95/00530 | 1/1995 | (WO). |

OTHER PUBLICATIONS

Relman, David A., "Molecular Phylogenic Analysis of Cyclospora, the Human Intestinal Pathogen, Suggests that It Is Closely Related to *Eimeria* Species," J. of Infectious Diseases 173:440–5 (1996).
Relman, David A., et al., "Molecular Phylogeny of the Intestinal Protozoan Pathogen Cyclospora," J. of Investigative Medicine Supp.2 43(2):221A (1995).
Tsolaki, A.G., et al., "Genetic Diversity at the Internal Transcribed Spacer Regions of the rRNA Operon among Isolates of *Pneumocystis carinii* from AIDS Patients with Recurrent Pnumonia," The Journal of Infectious Diseases 174:141–156 (1996).
Woese, C.J., et al., "Towards a natural system of organisms: Proposal for the domains Archaea, Bacteria, and Eucarya," Proc. Natl. Acad. Sci., USA 87:4576–4579 (1990).

Yoder, K.E., et al., "PCR–Based Detection of the Intestinal Pathogen Cyclospora," PCR Protocols for Emerging Infectious Diseases, ed. David H Persing, M.D., Ph.D., ASM Press (1996).
Landegren et al., A Ligase–Mediated Gene Detection Technique. Science 241 : 1077–1080 (1988).*
Mandell et al., Principles and Practrice of Infectious Diseases (4th edition). pp. 180–181. Churchill Livingstone, Inc., New York New York (1995).*
Baker, J.R., "The Origins of Parasitism in the Protists," International Journal for Parasitology 24(8): 1131–1137 (1994).
Barta, J.R., et al., "Evolutionary Relationships of Avian Eimera Species Among Other Apicomplexa Is Supported," Mol. Biol. Evol. 8:345–355 (1991).
Cai,J., et al., "PCR cloning and nucleotide sequence determination of the 18S rRNA genes and internal transcribed spacer 1 of the protozoan parasites *Cryptosporidium parvum* and *Cryptosporidium muris*," Biochemica et Biophysica Acta 1131: 317–320 (1992).
Carraway, M., et al., "Identification of Genetic Heterogeneity in the *Cryptospoidum parvum* Ribosomal Repeat," Applied and Environmental Microbiology 62(2): 712–716 (1996).
Colley, D.G., "Widespread Foodborne Cyclosporiasis Outbreak Present Major Challenges," Emerging Infectious Diseases 2(4):354356 (1996).
DeBoer, S.H., et al., "Attenuation of PCR inhibition in the presence of plant compounds by addition of BLOTTO," Nuc. Acids Res. 23(13):2567–2568 (1995).
Frothingham, Richard, and Kenneth H. Wilson, "Molecular Phylogeny of the *Mycobacterium avium* Complex Demonstrates Clinically Meaningful Divisions," The Journal of Infectious Diseases 169:305–312 (1994).
Gagnon, Steve, et al., "Molecular cloning, complete sequence of the small subunit ribosomal RNA coding region and phylogeny of *Toxoplasma gondii*," Molecular and Biochemical Parasitology 60:145–148 (1993).
Gajadhar, A.A., et al., "Ribosomal RNA sequences of *Sarcocystis muris*, *Theileria annulata*, and *Cryphecodinium cohnii* reveal evolutionary relationships among apicomplexans, dinoflagellates, and ciliates," Mol. and Biochem. Parasitology 45: 147–154 (1991).
Garcia–Lopez, H.L., et al., "Identification of Cyclospora in Poultry," Emerging Infectious Diseases 2(4):356–7 (1996).
Johnson, A.M., et al., "Phylogenic Relationships of Cryptosporidium Determined by Ribosomal RNA Sequence Comparison," International Journal for Parasitology 20(2): 141–147 (1990).

(List continued on next page.)

*Primary Examiner*—Ethan Whisenant
(74) *Attorney, Agent, or Firm*—Judy M. Mohr; Susan T. Evans; Elizabeth Arwine

(57) ABSTRACT

Nucleic acid-based methods for the detection of Cyclospora are disclosed, including PCR-based and hybridization-based techniques.

43 Claims, 4 Drawing Sheets

OTHER PUBLICATIONS

Langendijk, Petra S., et al. "Quantitative flourescence in situ hybridization of Bifidobacterium spp. with genus–specific 16S r RNA–targeted probes and its application in fecal samples," Applied and Environmental Microbiology 61(8): 3069–3075 (1995).

Lindsay, D.S., and K.S. Todd, Jr., "Coccidia of Mammals," *Parasitic Protozoa*, $2^{nd}$ edition, vol. 4, Julius P. Kreier, editor, Academic Press, Inc., 1993, pp. 89–131.

Lu, Jang–Jih, et al., "Typing of *Pneumocystis carinii* Strains with Type–Specific Oligonucleotide Probes Derived from Nucleotide Sequences of Internal Transcribed Spacers of rRNA Genes," J. of Clinical Microbiology, 33(11): 2973–2977 (1995).

Manz, Werner, et al., "Application of a suite of 16S r RNA–specific oligonucleotide probes designed to investigate bacteria of the phylum cytophaga–flavobacter–bacteroides in the natural environment," Micorbiology 142:1097–1106 (1996).

McLain, Denson Kelly, et al., "Variation in Ribosomal DNA Internal Transcribed Spacers 1 Among Eastern Populations of *Ixodes scapularis* (Acari: Ixodidae)," Journal of Medical Entomology 32(3):353–360 (1995).

Olsen, G.J., and C.R. Woese, "Ribosomal RNA: a key to phylogeny, " The FASEB Journal 7:113–123 (1993).

Ortega, Ynes R., et al., "Cyclospora Species—A New Protozoan Pathogen of Humans," The New England Journal of Medicine 328(18): 1308–1312 (1993).

"Outbreaks of *Cyclospora cayentanesis* Infection—United States, 1996," MMWR 45(25):549–551 (1996).

Pieniazek, N.J., et al., "PCR Confirmation of Infection with *Cyclospora cayetanensis*," Emerging Infectious Diseases 2(4):357–8 (1996).

* cited by examiner

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1747 base pairs
      (B) TYPE: nucleic acid
      (C) STRANDEDNESS: double
      (D) TOPOLOGY: linear (ii) MOLECULE TYPE: rDNA to rRNA (iii) HYPOTHETICAL: NO (iv) ANTI-SENSE: NO (vi) ORIGINAL SOURCE:
      (C) INDIVIDUAL ISOLATE: Cyclospora 18S rRNA sequence
      (GenBank U40261)

(xi) SEQUENCE DESCRIPTION: SEQ ID NO:1:

```
AGTCATATGC TTGTCTCAAA GATTAAGCCA TGCATGTCTA AGTATAAGCT TTTATACGGT      60

GAAACTGCGA ATGGCTCATT AAAACAGTTA TAGTTTATTT GATGGTCTCT TTTACATGGA     120

TAACCATGGT AATTCTATGG CTAATACATG CGCACAGGCC TCCTTCTTTG GAGGGGCCGT     180

GTTTATTAGA TACAAAACCA ACCCACTTTG TGGAGCCTTG GTGATTCATA GTAACCGAAC     240

GGATCGCATT TGGCTTTAGC CGGCGATAGA TCATTCAAGT TTCTGACCTA TCAGCTTTCG     300

ACGGTAGGGT ATTGGCCTAC CGTGGCATTG ACGGGTAACG GGGAATTAGG GTTCGATTCC     360

GGAGAGGGAG CCTGAGAAMC GGCTACCACA TCTAAGGAAG GCAGCAGGCG CGCAAATTAC     420

CCAATGAAAA CAGTTTCGAG GTAGTGACGA GAAATAACAA TACAGGGCAT TTAATGCTTT     480

GTAATTGGAA TGATAGGAAT TTAAAATCCT TCCAGAGTAA CAATTGGNGG GCAAGTCTGG     540

TGCCAGCAGC CGCGGTAATT CCAGCTCCAA TAGTGTATAT TAGAGTTGTT GCAGTTAAAA     600

AGCTCGTAGT TGGATTTCTG TCGTGGTCAT CCGGCCTTGC CCGTAGGGTG TGCGCCTGGG     660

TTGCCCGCGG CTTTTTTCCG GTAGCCTTCC GCGCTTCGCT GCGTGCGTTG GTGTTCCGGA     720
```

```
ACTTTTACTT TGAGAAAAAT AGAGTGTTTC AAGCAGGCTT GTCGCCCTGA ATACTGCAGC      780

ATGGAATAAT AAGATAGGAC CTTGGTTCTA TTTTGTTGGT TTCTAGGACC GAGGTAATGA      840

TTAATAGGGA CAGTTGGGGG CATTCGTATT TAACTGTCAG AGGTGAAATT CTTAGATTTG      900

TTAAAGACGA ACTACTGCGA AAGCATTTGC CAAGGATGTT TTCATTAATC AAGAACGACA      960

GTAGGGGGTT TGAAGACGAT TAGATACCGT CGTAATCTCT ACCATAAACT ATGCCGACTA     1020

GAGATAGGGA AACGCCTACC TTGGCTTCTC CTGCACCTCA TGAGAAATCA AAGTCTCTGG     1080

GTTCTGGGGG GAGTATGGTC GCAAGGCTGA AACTTAAAGG AATTGACGGA GGGGCACCAC     1140

CAGGCGTGGA GCCTGCGGCT TAATTTGACT CAACACGGGG AAACTCACCA GGTCCAGACA     1200

TGGGAAGGAT TGACAGATTG ATAGCTCTTT CTTGATTCTA TGGGTGGTGG TGCATGGCCG     1260

TTCTTAGTTG GTGGAGTGAT CTGTCTGGTT AATTTCGATA ACGAACGAGA CCTTAGCCTG     1320

CTAAATAGGA TCGGGAACCT TGGTTTCCGC ATCACTTCTT AGAGGGACTT TGCGTGTCTA     1380

ACGCAAGGAA GTTTGAGGCA ATAACAGGTC TGTGATGCCC TTAGATGTTC TGGGCTGCAC     1440

GCGCGCTACA CTGATGCATG CAACGAGTTT TTGACCTTGG CCGGCAGGTC TGGGTAATCT     1500

TTTGAGTGTG CATCGTGATG GGATAGATT ATTGCAATTA TTAATCTTCA ACGAGGAATG      1560

CCTAGTAGGC GCAAGTCAAC AGCTTGCGCC GATTACGTCC CTGCCCCTTG TACACACCGC     1620

CCGTCGCTGC AACCGATCGG AGGGTCCTGT GAACTCATTG GACTGACCAG CTNGTCTTCG     1680

CGGAGCTGGT CGGAAAGTTG CGTAAATAGA GCCCTCTAAA GGATGCAAAA GTCGTAACAC     1740

GGTTTCC                                                               1747

(2) INFORMATION FOR SEQ ID NO:2:

(i) SEQUENCE CHARACTERISTICS:
        (A) LENGTH: 1747 base pairs
        (B) TYPE: nucleic acid
        (C) STRANDEDNESS: double
        (D) TOPOLOGY: linear (ii) MOLECULE TYPE: rDNA to rRNA (iii) HYPOTHETICAL: NO (iv) ANTI-SENSE: NO (vi) ORIGINAL SOURCE:
         (C) INDIVIDUAL ISOLATE: Consensus Cyclospora 18S rRNA sequence (xi) SEQUENCE DESCRIPTION: SEQ ID NO:2:

AGTCATATGC TTGTCTCAAA GATTAAGCCA TGCATGTCTA AGTATAAGCT TTTATACGGT       60

GAAACTGCGA ATGGCTCATT AAAACAGTTA TAGTTTATTT GATGGTCTCT TTTACATGGA      120

TAACCATGGT AATTCTATGG CTAATACATG CGCACAGGCC TCCTTCTTTG GAGGGGCCGT      180

GTTTATTAGA TACAAAACCA ACCCACTTTG TGGAGCCTTG GTGATTCATA GTAACCGAAC      240

GGATCGCATT TGGCTTTAGC CGGCGATAGA TCATTCAAGT TTCTGACCTA TCAGCTTTCG      300

ACGGTAGGGT ATTGGCCTAC CGTGGCATTG ACGGGTAACG GGAATTAGG GTTCGATTCC       360

GGAGAGGGAG CCTGAGAAMC GGCTACCACA TCTAAGGAAG GCAGCAGGCG CGCAAATTAC      420

CCAATGAAAA CAGTTTCGAG GTAGTGACGA GAAATAACAA TACAGGGCAT TTAATGCTTT      480

GTAATTGGAA TGATAGGAAT TTAAAATCCT TCCAGAGTAA CAATTGGNGG GCAAGTCTGG      540

TGCCAGCAGC CGCGGTAATT CCAGCTCCAA TAGTGTATAT TAGAGTTGTT GCAGTTAAAA      600

AGCTCGTAGT TGGATTTCTG TCGTGGTCAT CCGGCCTTGC CCGTAGGGTG TGCGCCTGGG      660
```

```
TTGCCYGCGG CTTTYTTCCG GTAGCCTTCC GCGCTTCGCT GCGTGCGTTG GTGTTCCGGA        720

ACTTTTACTT TGAGAAAAAT AGAGTGTTTC AAGCAGGCTT GTCGCCCTGA ATACTGCAGC        780

ATGGAATAAT AAGATAGGAC CTTGGTTCTA TTTTGTTGGT TTCTAGGACC GAGGTAATGA        840

TTAATAGGGA CAGTTGGGGG CATTCGTATT TAACTGTCAG AGGTGAAATT CTTAGATTTG        900

TTAAAGACGA ACTACTGCGA AAGCATTTGC CAAGGATGTT TTCATTAATC AAGAACGACA        960

GTAGGGGGTT TGAAGACGAT TAGATACCGT CGTAATCTCT ACCATAAACT ATGCCGACTA       1020

GAGATAGGGA AACGCCTACC TTGGCTTCTC CTGCACCTCA TGAGAAATCA AAGTCTCTGG       1080

GTTCTGGGGG GAGTATGGTC GCAAGGCTGA AACTTAAAGG AATTGACGGA GGGGCACCAC       1140

CAGGCGTGGA GCCTGCGGCT TAATTTGACT CAACACGGGG AAACTCACCA GGTCCAGACA       1200

TGGGAAGGAT TGACAGATTG ATAGCTCTTT CTTGATTCTA TGGGTGGTGG TGCATGGCCG       1260

TTCTTAGTTG GTGGAGTGAT CTGTCTGGTT AATTTCGATA ACGAACGAGA CCTTAGCCTG       1320

CTAAATAGGA TCGGGAACCT TGGTTTCCGC ATCACTTCTT AGAGGGACTT TGCGTGTCTA       1380

ACGCAAGGAA GTTTGAGGCA ATAACAGGTC TGTGATGCCC TTAGATGTTC TGGGCTGCAC       1440

GCGCGCTACA CTGATGCATG CAACGAGTTT TTGACCTTGG CCGGCAGGTC TGGGTAATCT       1500

TTTGAGTGTG CATCGTGATG GGATAGATT ATTGCAATTA TTAATCTTCA ACGAGGAATG        1560

CCTAGTAGGC GCAAGTCAAC AGCTTGCGCC GATTACGTCC CTGCCCCTTG TACACACCGC       1620

CCGTCGCTGC AACCGATCGG AGGGTCCTGT GAACTCATTG GACTGACCAG CTNGTCTTCG       1680

CGGAGCTGGT CGGAAAGTTG CGTAAATAGA GCCCTCTAAA GGATGCAAAA GTCGTAACAC       1740

GGTTTCC                                                                 1747

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: primer 1FPL (xi) SEQUENCE DESCRIPTION: SEQ ID NO:3:

GCGGATCCGC GGCCGCTGGT TGATCCTGCC AGT                                      33

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: primer 152RPL (xi) SEQUENCE DESCRIPTION: SEQ ID NO:4:
```

GCGGATCCGC GGCCGCGCAG GTTCACCTAC                                              30

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: primer CYCF1E (xi) SEQUENCE DESCRIPTION: SEQ ID NO:5:

GGAATTCCTA CCCAATGAAA ACAGTTT                                                 27

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: primer CYCR2B (xi) SEQUENCE DESCRIPTION: SEQ ID NO:6:

CGGGATCCAG GAGAAGCCAA GGTAGG                                                  26

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: primer CYCF3E (xi) SEQUENCE DESCRIPTION: SEQ ID NO:7:

GGAATTCCTT CCGCGCTTCG CTGCGT                                                  26

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: primer CYCR4B (xi) SEQUENCE DESCRIPTION: SEQ ID NO:8:

CGGGATCCCG TCTTCAAACC CCCTACTG                28

DIAGNOSTIC METHODS FOR CYCLOSPORA

This application claims the benefit of U.S. Provisional Application No. 60/036,564, filed Jan. 29, 1997, incorporated herein by reference in its entirety.

At least one of the co-inventors of the present invention was supported in part by the U.S. Army Medical Component, Armed Forces Research Institute of Medical Sciences. Accordingly, the United States Government may have certain rights in this invention.

FIELD OF THE INVENTION

The present invention relates in general to diagnostic methods and compositions for the intestinal pathogen Cyclospora.

REFERENCES

Altschul, S. F., et al., *J. Mol. Biol.* 215:403–410 (1990).
Ashford, R. W., *Ann. Trop. Med. Parasitol.* 73:497–500 (1979).
Ashford, R. W., et al., *Lancet* 341:1034 (1993).
Ausubel, F. M., et al., *Current Protocols In Molecular Biology*, John Wiley and Sons, Inc., Media Pa. (1992).
Baker, J. R., Int. *J. Parasitol.* 24:1131–1137 (1994).
Barta, J. R., et al., *Mol. Biol. Evol.* 8:345–355 (1991).
Cai, J., et al., *Biochim. Biophys. Acta* 1131:317–320 (1992).
Carraway, M., et al., *Appl. Environ. Microbiol.* 62:712–716 (1996).
Centers for Disease Control and Prevention. Outbreaks of Cyclospora cayetanensis Infection, United States, *Morbid. Mortal. Week. Rep.* 45:549–551 (1996).
Cox, F. E. G., *Int. J. Parasitol.* 24:1301–1316 (1994).
DeBoer, S. H., et al., *Nuc. Acid Res.* 23:2567–68 (1995).
DeSoete, G., *Psychometrika* 48:621–626 (1983).
Dower, W. J., et al., U.S. Pat. No. 5,547,839 issued Aug. 20, 1996.
Ferre, F., et al., *Aids* 7(*Suppl* 2):S21–27 (1993).
Fodor, S. P. A., et al., U.S. Pat. No. 5,510,270 issued Apr. 23, 1996.
Fodor, S. P. A., et al., International Publication WO 95/00530, published Jan. 5, 1995.
Frothingham, R., and Wilson, K. H., *J. Infect. Dis.* 169:305–312 (1994).
Gagnon, S., et al., *Mol. Biochem. Parasitol.* 60:145–148 (1993).
Gajadhar, A. A., et al., *Mol. Biochem. Parasitol.* 45:147–154 (1991).
Hoge, C. W., et al., *Lancet* 341:1175–1179 (1993).
Hoge, C. W., et al., *Lancet* 345:691–693 (1995).
Johnson, A. M., et al., *Int. J. Parasitol.* 20:141–147 (1990).
Jukes, T. H., and Cantor, C. R., "Evolution of Protein Molecules," In: *Mammalian Protein Metabolism III* (Munro, H. N., Ed.) Academic Press, Inc., New York, N.Y. pp. 21–132 (1969).
Landegren, U., et al., *Science* 241:1077 (1988).
Landegren, U., et al., U.S. Pat. No. 4,988,617, issued Jan. 29, 1991.
Levine, N. D., in *Protozoan Parasites Of Domestic Animals And Of Man* (Second Ed.) Burgess, Minneapolis, Minn., pp. 406 (1973).
Lindsay, D. S., and Todd K. S. J., "Coccidia of Mammals," In: *Parasitic Protozoa Vol.* 4 (Krieier, J. P., Ed.) Academic Press, Inc., San Diego, Calif. pp. 89–131 (1993).
Long, E. G., et al., *J. Infect. Dis.* 164:199–202 (1991).
Lu, J. J., et al., *J. Clin. Microbiol.* 33:2973–7297 (1995).
Maidak, B. L., et al., *Nucl. Acids Res.* 22:3485–3487 (1994).
Manz, W., et al., *Microbiology* 142:1097–106 (1996).
McLain, D. K., et al., *J. Med. Entomol.* 32:353–360 (1995).
Medlin L., et al., *Gene* 71:491–499 (1988).
Mullis, K. B., et al., U.S. Pat. No. 4,683,195, issued Jul. 28, 1987.
Mullis, K. B., U.S. Pat. No. 4,683,202, issued Jul. 28, 1987.
Olsen, G. J., and Woese, C. R., *FASEB J.* 7:113–123 (1993).
Olsen, G. J., et al., *Comput. Appl. Biosci.* 10:41–48 (1994).
Ortega, Y. R., et al., *N. Engl. J. Med.* 328:1308–1312 (1993).
Ortega, Y. R., et al., *J. Parasitol.* 80:625–629 (1994).
Pape, J. W., et al., *Ann. Intern. Med.* 121:654–657 (1994).
Pieniazek, N. J., et al., *Emerging Infectious Diseases* 2:357–59 (1996).
Sambrook, J., et al., *Molecular Cloning: A Laboratory Manual,* Second Edition, Cold Spring Harbor Laboratory, Cold Spring Harbor, N.Y., (1989).
Sharrocks, A. D., "The Design of Primers for PCR" In: *PCR Technology—Current Innovations* (Griffin, H. G., and A. M. Griffin, Eds.) CRC Press, Boca Raton, Fla., pp. 5–11 (1994).
Sheather, A. L., *J. Comp. Pathol.* 36:266–275 (1923).
Shlim, D. R., et al.,*Am. J. Trop. Med. Hyg.* 45:383–9 (1991).
Swofford, D. L., in *PAUP: Phylogenetic Analysis Using Parsimony* (Version 3.0s) Illinois Natural History Survey, Champaign, Ill. (1991).
Todd, K. S., and Ernst, J. V., "Coccidia of Mammals except Man," In: *Parasitic Protozoa, Vol. III* (Kreier, J. P., Ed.) Academic Press, Inc., New York, N.Y. pp. 71–99 (1977).
Tsolaki, A. G., et al., *J. Infect. Dis.* 174:141–156 (1996).
Volkenandt, M., et al., *Proc. Soc. Exp. Biol. Med.* 200:1–6 (1992).
Weisburg, W. G., et al.,*J. Bacteriol.* 171:6455–6467 (1989).
Whiteley, N. M., et al., U.S. Pat. No. 4,883,750 (1989).
Winn-Deen, E., et al., *Clin Chem,* 37: 1522 (1991).
Woese, C. R., et al., *Proc. Natl. Acad. Sci. USA* 87:4576–4579 (1990).
Wu, D. Y., et al., *Genomics,* 4:560 (1989).
Wurtz, R., *Clin. Infect. Dis.* 18:620–623 (1994).

BACKGROUND OF THE INVENTION

Cyclospora is an emerging human intestinal pathogen (Ortega, et al., 1993, 1994). Since 1979, oocyst-like structures have been detected in the stool of humans with diarrhea (Ashford, 1979). These structures are spherical, 8–10 $\mu$m in diameter, autofluorescent, stain variably with acid-fast techniques, and contain clusters of membrane-bound globules. A variety of workers have referred to this organism as a blue-green alga (cyanobacterium-like body), a fungal spore, a coccidian-like body, and a large cryptosporidium (Long, et al., 1991; Ashford, et al, 1993). In 1993, in vitro sporulation and excystation of these cyanobacterium-like bodies revealed the presence of two sporocysts per oocyst and two sporozoites per sporocyst, leading to re-classification and naming of this organism as a species of the coccidian genus, Cyclospora (Ortega, et al., 1993, 1994).

Increasing numbers of reports suggest that this cyclosporan is an important cause of prolonged diarrheal disease in humans throughout the world (Wurtz, 1994). In one recent study, Cyclospora was found in fecal specimens from 11% of Haitians seropositive for the human immunodeficiency virus who had chronic diarrhea (Pape, et al., 1994). In most of these patients it was the sole pathogen identified and was detected repeatedly. Evidence favoring a role for this organism as a pathogen includes a significant association of oocysts with clinical illness (in absence of other known pathogens), clinical response to antimicrobial therapy, and clearance of organisms coincident with clinical resolution (Page, et al., 1994; Shlim, et al., 1991; Hoge, et al., 1993; Hoge, et al., 1995). Human cyclosporiasis is clinically indistinguishable, however, from cryptosporidiosis, isosporidiosis, giardiasis and microsporidiosis. Epidemiologic data indicate that the human-associated Cyclospora is transmitted by water and by food (Hoge, et al., 1993; Pieniazek, et al., 1996; Centers for Disease Control (CDC), 1996).

Prior to the discoveries disclosed herein, there was no simple way to conclusively diagnose Cyclospora infection in a primate, or to monitor water or food supplies for the presence of Cyclospora.

SUMMARY OF THE INVENTION

In one aspect, the present invention includes a method of detecting the presence of Cyclospora in a sample containing DNA. The method includes identifying, in the sample, the presence of a polynucleotide sequence which (i) is at least about 20 nucleotides in length, (ii) corresponds to a region of SEQ ID NO:2 which contains at least one discrimination position selected from the group consisting of positions at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694, (iii) contains the same nucleotide at such discrimination position as is contained in the corresponding discrimination position in a variant sequence defined by SEQ ID NO:2, and (iv) has a sequence that is greater than about 95% identical with a sequence defined by the corresponding region of SEQ ID NO:2. The presence of such a polynucleotide sequence in the sample indicates the presence of Cyclospora in the sample.

In general embodiments, the polynucleotide has a sequence that is greater than about 97% identical, or greater than about 98i identical, or greater than about 99% identical, or is simply 100% identical, with a sequence defined by the corresponding region of SEQ ID NO:2, such as SEQ ID NO:1.

The identifying may be performed using any of a variety of nucleic acid detection assays, including a hybridization detection assay, such as a hybridization assay performed on a substrate containing a plurality of different-sequence polynucleotide fragments. The different-sequence polynucleotide fragments may include, for example, target sequences for a plurality of different human intestinal pathogens. In one embodiment, the different-sequence polynucleotide fragments are arranged in a grid. In another embodiment, the substrate is a chip. The assay may be performed, for example, using a hybridization probe containing a region of SEQ ID NO:2 or SEQ ID NO:1 selected from the group consisting of regions defined by nucleotide positions 150–210, 240–280, 620–725, 1467–1518, and 1588–1700, or fragment of such a region, the fragment being at least about 20 nucleotides in length.

Another suitable nucleic acid detection assay employs polymerase chain reaction amplification. Such an amplification may be performed, for example, using a primer set in which at least one primer is designed such that the nucleotide at the 3' end of the at least one primer (i) corresponds to one of the discrimination positions, and (ii) is identical to the nucleotide at the corresponding discrimination position of SEQ ID NO:2.

An oligonucleotide ligation assay may also be used to identify the presence of Cyclospora in a sample containing DNA. Such an assay may be performed, for example, using a primer set in which the upstream primer is designed such that the nucleotide at the 3' end of the upstream primer (i) corresponds to one of the discrimination positions, and (ii) is identical to the nucleotide at the corresponding discrimination position of SEQ ID NO:2. Alternatively or in addition, the assay may be performed using a primer set in which one of the primers is designed to (i) span one of the discrimination positions, and (ii) fail to hybridize to its target if there are one or more mismatches between the one of the primers and its target.

In addition to the general and specific embodiments described above, the method may also be practiced in the context of the applicable general and specific embodiments detailed below.

In a related aspect, the invention includes another method of detecting the presence of Cyclospora in a sample containing DNA. This method includes (A) detecting, in the sample, a DNA fragment (i) having a sequence that is greater than about 20 nucleotides in length, (ii) corresponding to a region of SEQ ID NO:2 which contains at least one discrimination position selected from the group consisting of positions at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694, and (iv) having a sequence that is greater than about 95% identical with the sequence of the corresponding region of SEQ ID NO:2, and (B) identifying, in the DNA fragment, the presence of one or more of the following nucleotide bases at such discrimination position: position 155:C, position 178:C, position 249:T, position 258:A, position 62:G, position 328:T, position 473:A, position 495:A, position 501:T, position 507:T, position 636:C, position 60:G, position 667:G, position 698:G, position 706:C, position 831:G, position 1473:G, position 1579:A, position 1654:C, position 1659:T, position 1664:T, position 1674:G, position 1675:T, position 1684:A, or position 1694:A. The presence of such a base at the discrimination position in the DNA fragment indicates the presence of Cyclospora in the sample.

The above method may be practiced in the context of the general and specific embodiments already described above, and, as applicable, embodiments described below.

Also included in the invention is a method of detecting the presence of Cyclospora in a sample containing DNA. The method includes (A) amplifying the DNA by polymerase chain reaction (PCR) using a first primer set, consisting of a first primer and a second primer, where the primers are derived from SEQ ID NO:2 or SEQ ID NO:1, to generate a first set of amplification products, and (B) identifying, in the first set of amplification products, the presence of Cyclospora-specific 18S rRNA amplification products. The presence of such Cyclospora-specific 18S rRNA amplification products indicates the presence of Cyclospora in the sample.

In one embodiment, the primer set is selected to generate amplification products containing a sequence corresponding to the region of SEQ ID NO:2 between about nucleotides 420 and 1050. For example, the first primer may correspond to the region of SEQ ID NO:2 between about positions 418 and 436, and the second primer may correspond to the region of SEQ ID NO:2 between about positions 1035 and 1053. Specifically, the first primer may have the sequence provided as SEQ ID NO:5 and the second primer may have the sequence provided as SEQ ID NO: 6.

In a related embodiment, the primer set is selected to generate amplification products containing a sequence corresponding to the region of SEQ ID NO:2 between about nucleotides 685 and 980. For example, the first primer may correspond to the region of SEQ ID NO:2 between about positions 685 and 704, and the second primer may correspond to the region of SEQ ID NO:2 between about positions 959 and 978. Specifically, the first primer may have the sequence provided as SEQ ID NO:7 and the second primer may have the sequence provided as SEQ ID NO:8.

In a general embodiment, the Cyclospora is C. cayetanensis. In another general embodiment, the presence of Cyclospora-specific 18S rRNA amplification products is identified by analyzing the size distribution of the amplification products. In still another general embodiment, the sample (e.g., stool sample) is obtained from a human subject. Alternatively, the sample may be obtained from a food, such as a fruit (e.g., berry); a vegetable; or from a water supply.

The presence of Cyclospora-specific 18S rRNA amplification products may be identified by sequencing amplification products having a size expected from the relative locations of the first and second primers on SEQ ID NO:2.

The method may further include "nested" amplification, by (A) amplifying the first set of amplification products by polymerase chain reaction using a second primer set, consisting of a third primer and a fourth primer, where the third and fourth primers are derived from a region corresponding to the portion of SEQ ID NO:2 amplified by the first primer set, to generate a second set of amplification products, and (B) identifying, in the second set of amplification products, the presence of Cyclospora-specific 18S rRNA amplification products. The presence of such Cyclospora-specific 18S rRNA amplification products indicates the presence of Cyclospora in the sample. For example, the first primer set may be selected to generate amplification products containing a sequence corresponding to the region of SEQ ID NO:2 between about nucleotides 420 and 1050, and the second primer set may be selected to generate amplification products containing a sequence corresponding to the region of SEQ ID NO:2 between about nucleotides 685 and 980. In one embodiment, the first primer set consists of first and second primers which correspond to the region of SEQ ID NO:2 between about positions 418 and 436, and between about positions 1035 and 1053, respectively, and the second primer set consists of third and fourth primers which correspond to the region of SEQ ID NO:2 between about positions 685 and 704, and between about positions 959 and 978, respectively. Specifically, the first primer may have the sequence provided as SEQ ID NO:5, the second primer may have the sequence provided as SEQ ID NO:6, the third primer may have the sequence provided as SEQ ID NO:7 and the fourth primer may have the sequence provided as SEQ ID NO:8.

In another aspect, the invention includes a method of detecting the presence of Cyclospora in a sample containing DNA. The method includes (A) amplifying the DNA by polymerase chain reaction (PCR) using a first primer set, consisting of a first primer and a second primer, where the primers are designed to amplify a DNA fragment containing a sequence corresponding to SEQ ID NO:2 or a fragment thereof, to generate a first set of amplification products, and (B) identifying, in the first set of amplification products, the presence of Cyclospora-specific 18S rRNA amplification products. The presence of such Cyclospora-specific 18S rRNA amplification products indicates the presence of Cyclospora in the sample.

Also included is a method of detecting a Cyclospora infection in a human subject. Here, the method comprises (A) obtaining a sample from the subject, (B) isolating DNA-containing oocysts from the sample, (C) amplifying the oocyst DNA by polymerase chain reaction (PCR) using a first primer set, consisting of a first primer and a second primer, where the primers are derived from the sequence SEQ ID NO:2, to generate a first set of amplification products, and (D) identifying, in the first set of amplification products, the presence of Cyclospora-specific 18S rRNA amplification products. The presence of such Cyclospora-specific 18S rRNA amplification products indicates the presence of Cyclospora in the sample.

The sample may be, for example, a stool sample or a biopsy sample of the intestinal lining.

In another aspect, the invention includes a set of PCR primers suitable for the detection of Cyclospora. The set includes (A) a first primer having a sequence derived from a first region SEQ ID NO:2, and (B) a second primer having a sequence derived from a second region of SEQ ID NO:2. The 3' nucleotide of at least one of the primers corresponds to a discrimination position selected from the group consisting of positions in SEQ ID NO:2 at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694.

In a related aspect, the invention includes a set of PCR primers suitable for the detection of Cyclospora. The set includes (A) a first primer having a sequence selected from the group consisting of SEQ ID NO:5 and SEQ ID NO:7, and (B) a second primer having a sequence selected from the group consisting of SEQ ID NO:6 and SEQ ID NO:8.

Also included is a set of oligonucleotide ligation assay primers suitable for the detection of Cyclospora. The set includes (A) a first primer having a sequence derived from a first region of SEQ ID NO:2, and (B) a second primer having a sequence derived from a second region of SEQ ID NO:2. The first and second regions are adjacent one another on SEQ ID NO:2, and the sequence of the first primer spans at least one discrimination position selected from the group consisting of positions in SEQ ID NO:2 at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694.

In one embodiment, the first region is upstream the second region, and the at least one discrimination position corresponds to the 3' nucleotide of the first primer.

Also included is a DNA hybridization probe useful for the detection of Cyclospora in a sample. The probe contains a region of SEQ ID NO:2 selected from the group consisting of regions defined by nucleotide positions 150–210, 240–280, 620–725, 1467–1518, and 1588–1700, or fragment of such a region, the fragment being at least about 20 nucleotides in length.

These and other objects and features of the invention will become more fully apparent when the following detailed description is read in conjunction with the accompanying drawings.

DETAILED DESCRIPTION OF THE INVENTION

I. Definitions

When a first polynucleotide or polynucleotide fragment is said to "correspond" to a second polynucleotide or polynucleotide fragment, it means that the fragments are essentially co-extensive with one another when the sequences representing the fragments are aligned using a sequence alignment program, such as "MACVECTOR" (IBI, New Haven, Conn.) or a "BLAST" algorithm program (Altschul, et al., 1990). "Corresponding" polynucleotides or polynucleotide fragments typically contain a similar, if not identical, number of residues. However, corresponding polynucleotides or polynucleotide fragments may contain insertions or deletions of residues with respect to one another, as well as some differences in their sequences. The "sequence representing the fragment" in this context is understood to refer to the sequence of the fragment itself or to the complement or reverse complement of the sequence.

The percent identity (% identity) between two sequences is preferably calculated based on an optimal alignment of a single region of correspondence between sequences. No penalty is assigned for gaps introduced to obtain the optimal alignment. For example, if the sequences represent the same genes or sequence portions (e.g., 18S rRNA sequences) from two different species, and are of comparable length, the single region of correspondence is the entire sequence and the % identity is calculated based on an alignment of the complete sequences. Alternatively, if one complete sequence corresponds to a sub-region in the other sequence, the single region of correspondence is the region defined by the smaller sequence, and the % identity between the two sequences is calculated considering only the positions within this region of correspondence. The value of the % identity is calculated by counting the number of matches between the aligned sequences and dividing by the total number of residues in the region of correspondence.

Figure 2:
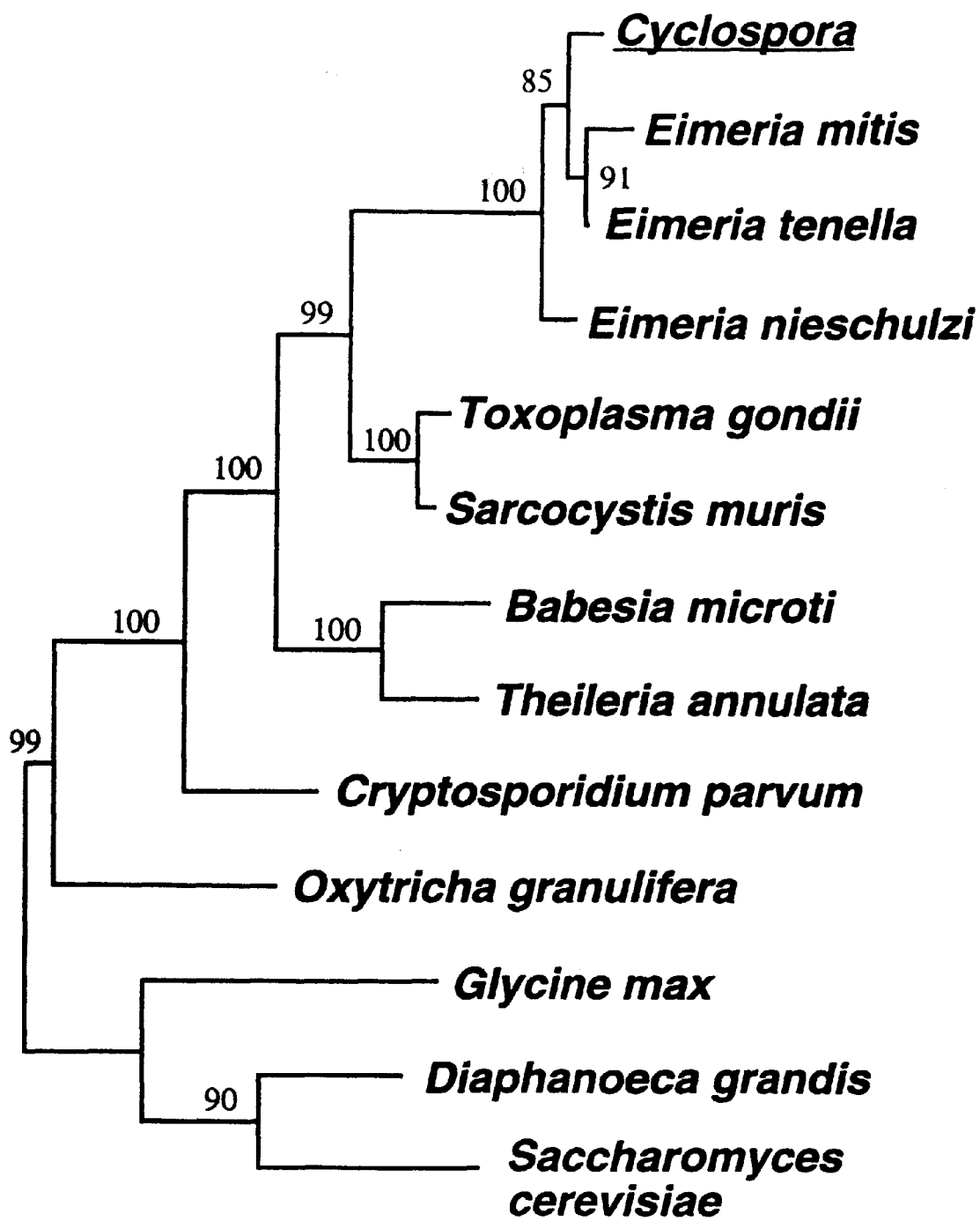
FIG. 2 is a phylogenetic tree generated using parsimony, based on 16S-like rDNA sequences. Horizontal line lengths are proportional to the number of steps assigned to topological elements in the tree.

Percent sequence similarity values (% similarity) are calculated in a similar fashion to that described above for identity, but with the specific modifications detailed in Example 4 and in reference to FIG. 2 and Table 2. Among these modifications was the restriction that alignments used in calculating the similarity and dissimilarity values were subject to constraints imposed by the positions of specific nucleotides in secondary structure models of the 18S rRNA. Percent sequence dissimilarity (% dissimilarity) is equal to 100 minus % similarity.

A "core sequence" is a sequence having at least one variable position represented by two or more individual residues. In a polynucleotide core sequence, such a variable position is indicated using the IUPAC degenerate code (e.g., "Y" represents "C" or "T/U"). Each core sequence defines two or more "variant sequences", or "variants", having a single nucleotide residue at each position. For example, the core sequence "AYG" defines the variant sequences "ACG" and "ATG". An exemplary core sequence is SEQ ID NO:2.

A polynucleotide sequence or fragment is "derived" or obtained from another polynucleotide sequence or fragment when it has the same sequence (or complement or reverse complement sequence) of nucleic acid residues as the corresponding region of the fragment from which it is derived.

A "primer set", with respect to oligonucleotide primers used in polymerase chain reaction (PCR; Mullis, 1987; Mullis, et al., 1987) experiments, refers to an upstream primer and a downstream primer which, when used in a PCR, are effective to generate a selected amplification product having the sequence of the target DNA between the regions on the target DNA which correspond to the primers. The upstream primer typically has a 5' to 3' sequence that is the same as that of the corresponding region on the target DNA, while the downstream primer typically has a 5' to 3' sequence that is the reverse complement of the corresponding region on the target DNA.

The terms "upstream" and "downstream" are used to refer to relative positions along a DNA sequence in the traditional sense—that is, in a polynucleotide sequence presented in the 5' to 3' direction (as are all sequences herein unless indicated otherwise) an "upstream" region is 5' of a "downstream" region.

A "target-specific amplification product" is a polynucleotide (e.g., DNA) amplified in a polynucleotide amplification reaction (e.g., PCR), where the polynucleotide corresponds in length and sequence to the region of target DNA that was to be amplified by the primer pair used in the PCR.

"Detecting the presence of Cyclospora in a sample" includes detecting the presence of Cyclospora oocysts, Cyclospora microorganisms and/or Cyclospora nucleic acids in such a sample.

A "Cyclospora-specific 18S rRNA amplification product" is a polynucleotide (e.g., DNA) amplified in a polynucleotide amplification reaction (e.g., PCR), where the sequence of the polynucleotide is greater than about 97% identical, preferably greater than about 98%, more preferably greater than about 996 identical, with the corresponding region of SEQ ID NO:2 or its complement or its reverse complement. In one embodiment, a "Cyclospora-specific 18S rRNA amplification product" is a polynucleotide (e.g., DNA) amplified in a polynucleotide amplification reaction (e.g., PCR), where the sequence of the polynucleotide is 100% identical, with the corresponding region of SEQ ID NO:2 or its complement or its reverse complement.

A "Cyclospora-specific 18S rRNA polynucleotide" is a polynucleotide (e.g., DNA), where the sequence of the polynucleotide is greater than about 97% identical, preferably greater than about 98% identical, more preferably greater than about 99% identical, with the corresponding region of SEQ ID NO:2 or its complement or its reverse complement. In one embodiment, a "Cyclospora-specific 18S rRNA polynucleotide" is a polynucleotide (e.g., DNA), where the sequence of the polynucleotide is 100% identical, with the corresponding region of SEQ ID NO:2 or its complement or its reverse complement.

II. Cyclospora

The present invention is directed, in one aspect, to a sequence-specific method for detecting Cyclospora, and in one particular embodiment, to a method for unequivocally discriminating between Cyclospora and a number of closely related potential intestinal pathogens (e.g., Eimeria). In yet another embodiment, the methods described herein are effective to discriminate between different species of Cyclospora. The methods described herein may also be used to discriminate between various host-associated Cyclospora and Cyclospora-like organisms.

The phenotypic classification and characteristics of this pathogen will now be described.

A. Host-Parasite Relationship

Structure and life cycle patterns have traditionally provided the framework on which taxonomic systems and theories of host-parasite relationships are based. Within the phylum Apicomplexa, the coccidia comprise a diverse collection of obligate intracellular parasites (Levine, 1973; Todd and Ernst, 1977). Among the coccidia, five genera (with the recent addition of Cyclospora) are known to infect humans and cause disease —Sarcocystis, Toxoplasma, Cryptosporidium, Isospora and Cyclospora. Sarcocystis and Toxoplasma require an intermediate host, while the others, such as Cyclospora, do not. Most coccidia penetrate and develop within intestinal epithelial cells and remain confined to the intestinal tract, although Toxoplasma and Sarcocystis have extraintestinal tissue phases in humans. *Cryptosporidium parvum* also displays tropism for extraintestinal sites (e.g. biliary tract). Cryptosporidium parvum is unusual, however, in that an external phase is not always required.

Sporulation characteristics distinguish the members of the family Eimeriidae. The members of this family include Eimeria, Cyclospora, and Isospora (Levine, 1973; Todd and Ernst, 1977). After a required period of time outside of the host during which sporogony takes place, the eimeriids are transmitted by ingestion of oocysts. Few species are adapted to extraintestinal host tissues.

Most coccidial infections in animals are asymptomatic, including those caused by Eimeria and Isospora spp. (Lindsay and Todd, 1993). Disease in humans and animals seems to occur as a result of relatively large doses of oocysts entering immunologically naive or immunosuppressed hosts. Migration, travel and large-scale farming practices facilitate these events. In fact, Eimeria spp. cause severe diarrheal disease and exert significant economic impact in many developed countries. They are also exceedingly host- and organ-specific. In general, the adoption of more than one host by a parasite may correlate with the ability to disseminate within a host and avoid an external phase, and may represent a more highly developed form of parasitism (Baker, 1994; Cox, 1994). Organisms currently defined as Eimeria spp. are not recognized as parasites of humans (Lindsay and Todd, 1993).

B. Classification of Cyclospora

Members of the Cyclospora genus were first described in 1870 in moles. Subsequently, they have been found in rodents, myriapods, and vipers (Lindsay and Todd, 1993). Cyclospora spp. are assigned to the family Eimeriidae on the basis of shared oocyst features, but they have been confused with other coccidians and more distant groups of organisms, as noted above. Nonhuman-associated cyclosporans are monoxenous and require an external phase.

Traditional coccidian classification schemes illustrate the confusing and sometimes contradictory nature of phenotypic characteristics. Schemes based on morphology (e.g., structural features of sporulated oocysts) and other phenotypes lack specificity and are sometimes misleading.

Experiments performed in support of the present invention and detailed below form the basis for nucleic-acid-based diagnostic assays for Cyclospora, and demonstrate that the human-associated parasite, *C. cayetanensis*, is closely related to the genus, Eimeria. The data disclosed herein further indicate that Cyclospora is as closely-related to various Eimeria spp. as some Eimeria spp. are to other Eimeria spp. It is contemplated that *C. cayetanensis* is also closely-related to Isospora, and that methods described herein for detection of Cyclospora may also be applied to the detection of Isospora. Moreover, the results described herein allow the identification of 18S rDNA regions that are effective to discriminate between the human associated and other host-associated Cyclospora and Cyclospora-like organisms (e.g., baboon).

The results described herein are surprising and unexpected, because based on traditional morphologically-based classification schemes, Cyclospora was thought to be more closely related to Cryptosporidium than to Eimeria spp.

C. Implications of the New Classification

While not wishing to be bound by any particular mechanism, it will be appreciated that molecular phylogenies offer the possibility of predicting biological behavior from evolutionary relationships. In this context, the finding of close relationships among Cyclospora and Eimeria spp. raises several implications. This cyclosporan may be an exception to the rule that most human intestinal protozoan parasites are infective upon excretion. This possibility assumes that Cyclospora sporulation takes place outside of the human host. The life cycle and phylogenetic relationships of the human commensal and occasional pathogen, *Isospora belli* are unclear, but unsporulated oocysts are passed in stool. The data presented herein suggest that because Cyclospora is not clearly related to the tissue-invading coccidia, Sarcocystis and Toxoplasma, it may not have a tissue phase and may be directly transmitted.

III. Detection of Cyclospora

The present invention provides methods for the detection of Cyclospora nucleic acids in nucleic acid-containing samples. Samples for use in the present method include any source suspected of infection by Cyclospora. A sample may be, e.g., a stool sample or a biopsy sample from the intestinal lining of a human or other host, such as a baboon, from a fruit (e.g., berry) or vegetable, or any potential food source, and/or water supply. Generally, the sample is screened for the presence of sequences that correspond to and/or are derived from a sequence containing or contained in SEQ ID NO:2.

As applied to the present invention, DNA is isolated, for example, as described in Example 2 from oocysts isolated as described in Example 1.

Briefly, oocysts are first isolated from a sample suspected of Cyclospora infection as described in Example 1 (A.1.). Alternatively, oocyte fecal specimen samples may be prepared by first mixing a slurry of the fecal material with an equal volume of 2.5% potassium dichromate solution, followed by straining the resulting mixture through sterile cotton gauze sponges, and rinsing thoroughly with water to release any trapped oocysts. The sample is then allowed to stand at room temperature to sediment the debris, followed by removal of the upper layer of fluid containing the majority of the oocysts. The remaining oocysts are then obtained by adding an equal volume of an organic solvent such as chloroform or ethyl ether, and vigorously mixing, The sample is then allowed to separate. The oocysts are retained in the aqueous phase while lipid material is extracted into the organic layer. The oocyst-containing fractions are then combined and the oocysts are then washed with water, and centrifuged, e.g., at 1,000×g for 15 min.

Following oocyst isolation, the oocysts are typically further purified, e.g., using Sheather's sugar flotation procedure (Sheather, 1923) and cesium chloride step gradient centrifugation, as described in Example 1 (A.2 and A.3).

Cesium chloride gradient purification may be advantageous in the purification of oocysts from fecal material, since fecal samples often contain substances which can inhibit PCR. In instances where cesium chloride purification is not possible, dilution of the samples prior to sonication or glass bead disruption can be employed to minimize this problem.

Illustrative isolation and purification of DNA from suspected Cyclospora-contaminated food samples, e.g., fruit, is described in Example 1.B.

Following Cyclospora oocyst purification, the oocysts may be prepared for PCR or any hybridization and/or amplification assay described herein using any of several methods well known in the art, for example, mechanical lysis of the cell wall with glass beads or disruption by sonication (Example 2). Bath sonication generally represents a more reproducible method than glass bead disruption, however, bath sonication is more prone to cross-contamination of the samples. To minimize the potential for cross-contamination, "PARAFILM" or a similar material is used to seal the tubes prior to sonication.

Such DNA samples, e.g., sequences suspected to be Cyclospora specific sequences, may be detected using any of a variety of DNA hybridization and/or amplification methods well known in the art, such as the exemplary methods described below.

A. PCR Detection of Cyclospora

An exemplary approach to detecting the presence of a given sequence or sequences in a polynucleotide sample involves selective amplification of the sequence(s) by polymerase chain reaction (Mullis, 1987; Mullis, et al., 1987). In this method, primers complementary to opposite end portions of the selected target sequence(s) are used to promote, in conjunction with thermal cycling, successive rounds of primer-initiated replication.

In the context of the present invention, the target sequences are genomic sequences in the region of the genome encoding ribosomal RNAs (rRNAs) and/or the rRNAs themselves (which may be amplified using reverse-transcriptase (RT) PCR, (Ferre, et al., 1993; Volkenandt, et al., 1992)). Exemplary target sequences include the genomic DNA encoding the 16S-like (18-S) rRNA (rDNA) of Cyclospora. As detailed below in Example 3, selected sequences in the rDNA are amplified by polymerase chain reaction (PCR) using a primer set which consists of an upstream and downstream primer whose sequences are selected to amplify a desired fragment containing or contained in the sequence provided as SEQ ID NO:2. The size distribution of the amplification produced in such a reaction is then determined, typically by resolving the amplification products on a gel and staining for DNA (e.g., with ethidium bromide). If desired, amplification products in the expected size range can then be isolated (e.g., excised from the gel), and sequenced (or cloned and sequenced).

The sample is identified as containing Cyclospora organisms, oocysts or nucleic acids if the amplification products are Cyclospora-specific 18S rRNA amplification products that correspond to the portion of SEQ ID NO:2 between the regions corresponding to the PCR primers. Cyclospora-specific 18S rRNA amplification products are DNA fragments which have greater than about 97%, preferably greater than about 98%, identity to the corresponding region of SEQ ID NO:2. In a specific embodiment, the amplification products are DNA fragments which have greater than about 97%, preferably greater than about 98%, identity to the corresponding region of SEQ ID NO:1.

In cases where the sample is obtained from a human subject suffering from clinical symptoms consistent with Cyclospora infection, the diagnosis may be made by simply assaying for the presence of PCR products in the expected size range. Because humans are not known to be infected with Eimeria, there is no need to sequence the amplification products.

In cases where the sample being assayed is a water or food sample, which could be contaminated by Cyclospora and/or Eimeria, the mere presence of amplification products obtained using primers which can amplify both Eimeria and Cyclospora sequences may not be sufficient to distinguish between these two types of pathogens, and such PCR products would need to be evaluated further. Examples of such further evaluation include sequencing of the products, detection by hybridization using Cyclospora-specific hybridization probes (see, e.g., Example 6), or restriction fragment length polymorphism (RFLP) analyses of the amplification products. In the latter approach, the analysis typically relies on variations in the lengths of DNA fragments produced by restriction enzyme digestion. The polymorphisms or mismatches identified are typically referred to as restriction fragment length polymorphisms or RFLPs. Methods for conducting such analyses are known in the art (e.g., Ausubel, et al., 1992).

PCR primers may also be selected to amplify only Cyclospora and not, e.g., Eimeria. Exemplary primer sets effective to selectively amplify Cyclospora sequences include primers having a 3' end nucleotide which corresponds to one of the positions in the Cyclospora 18S rRNA sequence which differs between Cyclospora and Eimeria sequences, where the identity of the 3' nucleotide is that of the corresponding nucleotide in SEQ ID NO:2. As detailed in Example 6, such positions include the following (numbering refers to positions in SEQ ID NO:1): 155, 178, 249, 258, 262, 328, 473, 495, 501, 507, 636, 660, 667, 698, 706, 831, 1473, 1579, 1654, 1659, 1664, 1674, 1675, 1684 and 1694.

Since amplification products are generally not obtained in cases where the 3' end of the primer is not matched with the target sequence, the primers are not expected to amplify Eimeria sequences, but are expected to amplify Cyclospora sequences. Accordingly, the presence of Cyclospora in a sample may be assayed with such primers simply by detecting the presence of an appropriately-sized DNA product, without need for subsequent (e.g., sequence) analysis of the amplification product.

Multiplex PCR methods may also be employed to detect Cyclospora according to the methods of the invention. In multiplex PCR, several different primer pairs are used in a single PCR reaction to generate different sets of specific amplification products. At least one primer of each primer set typically contains a unique label, such as a fluorescent probe which emits at a distinct wavelength, enabling the differentiation of different sets of amplification products amplified by the different primer sets. The different primer sets may be directed to different types of pathogens responsible for, e.g., diarrhea, to DNA sequences of closely related pathogens to allow positive identification of one type versus another (e.g., one primer set designed to amplify both Eimeria and Cyclospora sequences, a second set designed to amplify only Eimeria sequences, and a third set designed to amplify only Cyclospora sequences), or to DNA sequences within a single species which allow it to be detected both generically, as well as allowing a determination of a particular isolate (e.g., primer set designed to detect any Cyclospora isolate, and primer sets capable of selectively amplifying specific Cyclospora isolates). Such primer sets may be readily designed based on the Cyclospora-specific nucleotide regions disclosed herein, coupled with known sequence information for other suspected intestinal pathogens.

B. Hybridization-Based Detection of Cyclospora

In cases where the number of organisms is not limiting (e.g., in the stool of an individual with an acute Cyclospora infection), hybridization approaches may be used to detect the presence of Cyclospora. For example, such hybridization-based methods can be used to detect Cyclospora infection in human patients having clinical symptoms consistent with Cyclospora infection. If the patients are indeed ill from Cyclospora, their stool should contain a sufficiently large number of organisms to confirm a diagnosis based on the results of a hybridization assay.

Traditional hybridization methods are typically less sensitive than amplification-based methods such as PCR. However, such hybridization assays are not sensitive to inhibitors of PCR that are often present in fecal or lystate samples, and may, depending on the assay, be easier to perform and be faster and more economical.

Hybridization methods for detection of Cyclospora are particularly advantageous in cases where the assayed sample is not expected to contain Eimeria spp., (i.e., well-suited for detection of Cyclospora infection in samples from humans) since it is not typically straightforward to determine the sequence of the fragments in the sample responsible for a positive hybridization signal.

One suitable hybridization method is Southern blotting. In this method, DNA fragments in the sample are fractionated by gel electrophoresis, then fixed on a nylon or nitrocellulose filter. By reacting the filter with one or more labeled probes (e.g., probes derived from SEQ ID NO:2) under hybridization conditions, the presence of bands containing the probe sequence can be identified. The method is especially useful for identifying fragments in a restriction-enzyme DNA digest which contains a given probe sequence.

As applied to the present invention, DNA is isolated, for example, as described in Example 2 from oocysts isolated as described in Example 1. The DNA is then digested with selected restriction enzymes, resolved on a gel (e.g., polyacrylamide gel), and blotted using standard methods (e.g., Ausubel, et al., 1992; Sambrook, et al., 1989). The blot is then probed with a labelled fragment having a sequence derived from SEQ ID NO: 2 using known techniques.

Hybridization probes used in the practice of the invention may be labelled using, e.g., a radiolabel or a fluorescent reporter (e.g., fluorescein). The use of fluorescent reporters for detection of species-specific sequences is known (e.g., Manz, et al., 1996, incorporated herein by reference).

Hybridization technology may also be employed in the context of an assay performed on a substrate containing a plurality of different-sequence polynucleotide fragments. In one embodiment, the different-sequence polynucleotide fragments are arranged in a grid on the surface of a chip, such as a silicon wafer, in which the identity of the polynucleotide fragment at each site is known. The sequences of the different-sequence polynucleotide fragments may include, for example, sequences for a plurality of different human intestinal pathogens (e.g., corresponding to a region or regions of core SEQ ID NO:2 containing one or more of the discrimination positions described herein), and the "assay chip" may be used to diagnose the presence of and, if desired, the relative level of, DNA sequences from most, if not all, known human pathogens detectable in, e.g., a stool sample, which can cause diarrhea. The synthesis of such chips is known (e.g., Fodor, et al., 1996, incorporated herein by reference), as is the use of such chips for detection of selectively-hybridizing DNA oligomers (e.g., Fodor, et al., 1995, herein incorporated by reference).

A labeled target DNA sample, such as that obtained from a human or food sample suspected of Cyclospora infection, or infection by any of a number of gastrointestinal pathogens, is then hybridized to the array, and the resulting pattern is examined to determine the identity of complementary probes in the array. Such selective hybridization may be used to simply detect the presence of a target polynucleotide or DNA oligomer in the test sample and/or to determine the sequence of such a target polynucleotide (see, e.g., Dower, et al., 1996, incorporated herein by reference).

Human pathogens (in addition to Cyclospora) which can cause diarrhea and which the assay may be designed to detect include, but are not limited to, the following (*Infections Of The Gastrointestinal Tract*, Blaser, M. J., et al., Eds., Raven Press, New York, 1995, incorporated herein by reference): Viruses, such as Rotavirus, Cytomegalovirus, Adenovirus, Astrovirus, Picobirnavirus, Norwalk virus and Norwalk-like viruses; bacteria, such as *Aeromonas hydrophila, Campylobacter jejuni, Clostridium difficile,* Dysgonic fermenter-3, Enteropathogenic *E. coli, Mycobacterium tuberculosis, Atypical mycobacteria,* Plesiomonas, Salmonella, Whipple's disease bacillus, Yersinia, *Vibrio cholerae,* and many other enteric bacteria; Fungi, including Candida; and Parasites, such as Cyclospora, *Blastocystis hominis,* Cryptosporidium, *Entamoeba histolytica, Giardia lamblia, Giardia duodenalis, Isospora belli,* Microsporidia, Strongyloides, and Hookworm. Organisms indicated in bold result in infections in normal hosts; the other organisms typically attack only immunosuppressed individuals.

Specific polynucleotide probes for many of the pathogens listed above are known, and may be employed by one of skill in the art in conjunction with the teachings herein to make an assay which facilitates the clinical diagnosis of a patient with diarrhea.

C. Ligation-Based Detection of Cyclospora

Methods of identifying known target sequences by probe ligation methods are known (Wu, et al., 1989; Whiteley, et al., 1989; Landegren, et al., 1988, 1991; Winn-Deen, et al., 1991). In one approach, known as oligonucleotide ligation assay (OLA), two probes or probe elements which span a target region of interest are hybridized with the target region. Where the probe elements match (basepair with) adjacent target bases at the confronting ends of the probe elements, the two elements can be joined by ligation, e.g., by treatment with ligase. The ligated probe element is then assayed, evidencing the presence of the target sequence. If the 3' end of the upstream probe does not match the target sequence, the ligation reaction fails, and no ligated probe elements are detected (Landegren, et al., 1991, incorporated herein by reference).

Such an oligonucleotide ligation assay may be used to differentiate Cyclospora sequences from other closely-related sequences, such as Eimeria sequences, by designing the probes to span a region of SEQ ID NO:2 which contains a position that has a different nucleotide in the Cyclospora sequence than in Eimeria sequences. Such "discriminating" positions are identified below, e.g., in Example 6. The probes are designed so that the 3' end of the downstream probe corresponds to a selected discriminating position, and the 5' end of the upstream probe corresponds to the nucleotide immediately downstream of the selected discriminating position, essentially as described in Landegren, et al., 1991.

The sequences of the probes are preferably selected so that they form perfect hybrids with Cyclospora sequences (corresponding regions of SEQ ID NO:2), but so that at least the 3' end of the upstream probe contains a mismatch with respect to corresponding positions in Eimeria sequences. The oligonucleotide ligation assay is then applied to a test sample, and ligated oligonucleotides are detected using known methods (e.g., as described in Landegren, et al., 1991).

In a modification of this approach, termed Ligase Chain Reaction (LCR), the ligated probe elements act as a template for a pair of complementary probe elements. With continued cycles of denaturation, reannealing and ligation in the presence of the two complementary pairs of probe elements, the target sequence is amplified geometrically, allowing very small amounts of target sequence to be detected and/or amplified (Winn-Deen, et al., 1991, incorporated herein by reference). The presence of Cyclospora in a test sample is detected using LCR essentially as described above for OLA, followed by the geometric amplification.

It will be appreciated that the above illustrations serve to illustrate, but not limit, the types of hybridization, amplification, and/or ligation approaches which are available in the art for the detection of selected polynucleotide sequences in a test sample, and which may be used in conjunction with the teachings herein in the practice of the invention.

D. Additional Assays—"Fingerprinting" different Cyclospora Isolates

In another aspect, the invention includes a method of distinguishing individual cyclospora isolates from one another. This aspect is based on the sequence analysis of two intergenic or internal transcribed spacer (ITS) sequences, located immediately downstream from the 18S rDNA, upstream from the 28S rDNA, and separated by the 5.8S rDNA. Because they are not coding sequences, ITS regions have accumulated more mutations over time than have the rDNA sequences, and hence, are more variable. The ITS1 region (approximately 660 bp) has been amplified and cloned from 5 isolates. Sequence data from three Nepalese isolates suggest that there may be as many as 31 positions of heterogeneity (~4% variability) among these isolates (while there are only 5 variable positions among different clones from the same patient sample). These data indicate that the Cyclospora ITS1 may be an informative and useful sequence target for the "fingerprinting" of different Cyclospora isolates. The ITS sequences may be detected in or amplified from selected samples essentially as described below for 18S rRNA sequences.

The ability to "fingerprint" Cyclospora isolates permits the practitioner of the invention to determine the relationships among Cyclospora isolates from patients in different regions of the United States, relationships between patient Cyclospora isolates and those that may be found in food or water, and the relationships between these U.S. isolates and those found in other parts of the world. This information enables the tracing of transmission routes, and can provide information on whether patients can be infected with more than one isolate. Further, the data can demonstrate whether certain isolates or groups of isolates are associated with different forms of disease, and/or with environmental versus clinical reservoirs.

IV. Additional Applications

The sensitive PCR assay described herein may be used to detect Cyclospora contamination of (i) food, such as fruit (e.g., berries) and vegetables, (ii) water (such as contamination of municipal water supplies), and (iii) clinical diagnoses of Cyclospora infection.

Fruits which may be screened for contamination by Cyclospora include, but are not limited to berry-like fruits, such as Vitis (grapes), Fragaria (strawberries), Rubus (raspberries, blackberries, loganberries), Ribes (currants and gooseberries), Vaccinium, (blueberries, bilberries, whortleberries, cranberries), and Actinida (kiwifruit and Chinese gooseberry). Further, other fruits, including, but not limited to, Malus (apple), Pyrus (pears), most members of the Prunus genera, sapota, mango, avocado, apricot, peaches, cherries, plums, and nectarines may also be screened using the methods of the invention.

In screening fruits, the oocysts are prepared essentially as described below for berries in Example 1.B., and the PCR is carried out essentially as described below, with the exception that approximately 2 $\mu$L of a 50 mg/ml instant nonfat dry milk suspension are added to approximately a 20 $\mu$L sample of fruit lysate. This step is performed to attenuate inhibition of the PCR reaction caused by endogenous inhibitory plant compounds (DeBoer, et al., 1995).

The following examples illustrate but in no way are intended to limit the present invention.

Materials and Methods

Unless otherwise indicated, restriction enzymes and DNA modifying enzymes were obtained from New England Biolabs (Beverly, Mass.) or Boehringer Mannheim (Indianapolis, Ind.). "UltraPURE" agarose was obtained from Gibco/BRL (Gaithersburg, Md.). Other chemicals were purchased from Sigma (St. Louis, Mo.) or United States Biochemical (Cleveland, Ohio).

A. Buffers

The following buffer solutions were utilized.

Phosphate-buffered saline (PBS)

10× stock solution, 1 liter:

80 g NaCl 2 g KCl 11.5 g $Na_2HPO4\text{-}7H_2O$ 2 g $KH_2PO_4$

Working solution, pH 7.3:

137 mM NaCl 2.7 mM KCl 4.3 mM $Na_2HPO_4\text{-}7H_2O$ 1.4 mM $KH_2PO_4$

Sucrose Solution 500 g sucrose 320 ml water 6.5 g phenol

Tris Buffer (pH 7.2)

50 mM Tris 10 mM EDTA

TE Buffer (pH 8.0)

10 mM Tris 1 mM EDTA

CsCl Solutions

Stock solution:

specific gravity 1.8 (1.8 g/ml)

CsCl solution 1:

48 ml Tris buffer, 48 ml CsCl stock solution

CsCl solution 2:

84 ml Tris buffer, 12 ml CsCl stock solution

CsCl solution 3:

90 ml Tris buffer, 6 ml CsCl stock solution

10× PCR Buffer 100 mM TrisHCl (pH 8.5)

20 mM MgCl2

500 mM KCl

PCR Master Mix

10 $\mu$l of 10× PCR Buffer

2 $\mu$l of 40 mM dNTPs (10 mM each)

20 pmol each of two PCR primers
5% glycerol
water to 80–85 μl per reaction
10% Laureth 12
10 g Laureth 12 (PPG Industries, Gurnee, Ill.)
90 ml sterile ddH$_2$O
Microwave 2×30 sec to melt the Laureth. Add a stir bar, mix and aliquot 10 ml per 15 ml tube. Freeze protected from light.
1×TE, pH 7.4+0.1% Laureth 12
10 ml 1M Tris, pH 7.4 (Digene #3400-1042)
2 ml 0.5 M disodium EDTA, pH 8.0 (Digene #3400-1003)
10 ml 10% Laureth 12
sterile deionized water to 1 L.
1×TE, pH 7.4+1.0% Laureth 12
1 ml 1M Tris, pH 7.4
0.2 ml 0.5 M disodium EDTA, pH 8.0
10 ml 10% Laureth 12
sterile deionized water to 100 ml.

EXAMPLE 1

Isolation and Purification of Cyclospora oocysts

A. Isolation from Fecal Specimens

Fecal specimens were collected at several clinics, including the CIWEC clinic in Kathmandu, Nepal, from patients with watery diarrhea or diarrheal disease, and screened microscopically for cyclosporan oocysts. Positive specimens that had no evidence of other known diarrheal disease agents were selected for further study. Oocysts were purified from the positive specimens as described below. Fecal specimens were handled and oocysts purified at locations physically distant from the sites of further analysis.

1. Oocyst Isolation

Specimen samples were typically prepared by diluting the positive fecal specimens in 2.56 potassium dichromate (K$_2$Cr$_2$O$_7$) solution and straining the resulting solution through wire sieves or cotton gauze to remove large debris.

2. Purification of Oocysts: Sugar Flotation Method

Oocysts isolated as described above were subjected to a modification of Sheather's sugar flotation procedure (Sheather, 1923). In some cases, three sugar solutions of different densities were employed for improved separation and concentration of oocysts.

Briefly, the volume of the oocyst pellet was estimated and the oocysts were resuspended in an equal volume of water. 40 ml of the sucrose solution were mixed with 10 ml of the oocyst-water suspension. The mixture was inverted 5 times and centrifuged at 200×g for 20 min at 15° C.

The mixture was then overlaid with water, resulting in a whirlpool action which caused the oocysts to rise into the water layer. A drop of the overlaid water was examined for oocysts. In samples containing oocysts, the overlay water (containing the oocysts) was removed and saved. The harvest was repeated, and the oocysts were washed several times with water by centrifugation at 1,000×g for 10 min at 15° C.

Samples isolated as described in this step may be used for diagnostic analyses (e.g., prepared for PCR), or may be further purified, using, e.g., a cesium chloride (CsCl) gradient.

3. Purification of Oocysts: CsCl Gradient Method

The CsCl solutions described in the Materials and Methods were layered in 50-ml Sepcor tubes (Labcor Products, Inc.) as follows: 12 ml of CsCl solution 1, followed by 12 ml of CsCl solution 2 and then 12 ml of CsCl solution 3. Five ml of the oocysts in Tris buffer were then layered on top of the gradient, and the tubes were centrifuged at 16,000×g for 60 min at 4° C.

Following centrifugation, the tubes contained three bands and a pellet. The oocysts, present between the top and middle layers (or between layers with densities of 1.1 and 1.05 g CsCl per ml), were aspirated out using a 12-ml "LUER-LOK" syringe with an 18-gauge needle and washed in 5 volumes of water at least four times by centrifuging at 1,000×g for 10 min at 15° C. The oocysts were then stored at 4° C. in 2.5% K$_2$Cr$_2$O$_7$.

The sucrose flotation and CsCl gradient centrifugation methods described above concentrated the oocysts to approximately 2×10$^5$/ml. The organisms ranged in size from 8–10 μm in diameter and shared structural features consistent with those previously reported for the oocysts of human-associated Cyclospora (Ortega, et al., 1993, 1994).

B. Isolation from Berries

Cyclospora oocytes were isolated from berries according to one of the following protocols.

1. Template Preparation:

Approximately 300 ml of TE-0.1% Laureth 12 was aliquoted into a "ZIPLOCK" bag to which was added about 250 gm of berries. The berries were not cut or sliced, due to the inhibitory effect of berry juice on PCR. The resulting mixture was then agitated gently for approximately 10 min by placing on a platform shaker set at about 60 cycles per min. A corner of bag was then cut and the liquid suspension was drained into a beaker. The liquid suspension was then poured through stacked 5 inch #40 and #60 mesh sieves nested in a funnel, leaving large particulate matter in the beaker.

Two 45 ml portions of the sterile liquid suspension were then decanted into 50 ml centrifuge tubes (Gibco #925-4900XT), followed by a thorough wash in detergent. The samples were rinsed 5× (including at least 2× in deionized water) and drained). Remaining suspension (approx. 200 ml) was stored at 4° C. for later analysis.

The two tubes were then centrifuged at 1500×g for 10 minutes at 4° C. using a swinging bucket rotor. The supernatant was then removed by decanting or aspiration, leaving 1–2 ml per tube of supernatant and pellet fractions containing the oocysts. The volume of residual supernatant and pellet fraction varied, depending on the type and condition of berries. The residual supernate was then used to resuspend sediment from the second tube for PCR analysis. The sediment was then distributed evenly into 1.5 ml microcentrifuge tubes.

The tubes were then spun in a microcentrifuge at 10,000 RPM for 10 min. The supernatants were then decanted and discarded. The samples were consolidated by resuspending all of the pellets into a total of one ml of 1× TE in a 1.5 ml microcentrifuge tube. The combined samples was then spun in a microcentrifuge at 10,000 RPM for 10 min, followed by removal of the supernatant. The resulting pellet was then resuspended in 300 ul of TE-1.0% Laureth 12.

2. Template preparation:

100 μL of berry sediment was washed four times with an equal volume of 1× PCR Buffer I. Each washing consisted of vortexing sediment followed by centrifuging at 14,000 RPM for 3 minutes. Supernatant was removed and the pellet was retained for the next washing. The final pellet was resuspended in 100 μL 1× PCR Buffer I.

EXAMPLE 2

PCR Target Preparation

The oocysts used to generate the results shown herein were typically prepared using the protocols described below.

A. Glass Beads

A 0.1 ml aliquot of the oocyst suspension was washed with 0.5 ml of TE by centrifuging at 550×g for 3 min. The wash was repeated two or three times, and 0.2 ml of TE along with about 0.45 ml of glass beads (425–600 µm; Sigma no. G-8772) was added. The suspension was placed on ice for 5 min, shaken by hand vigorously for 2 min, and placed on ice for 5 min. The suspension was then centrifuged at 8,500×g at 4° C. for 3 min. The supernatant was then diluted 1:10 for PCR, and ~1 ml of this dilution was used for PCR amplification.

B. Sonication

500 µl of the sucrose flotation or 100 µl of the cesium chloride gradient purification samples were centrifuged at 1,000×g at 4° C. for 30 min. The oocysts were resuspended in 70 µl of TE, and this suspension was diluted 1:10 and 1:100 in TE in 1.5-ml snap-top Eppendorf tubes to a final volume of 100 µl.

The concentrated sample and the diluted samples were wrapped with "PARAFILM" (to reduce chance of contamination) and sonicated for 2 min at 120 W in a bath sonicator (Branson Cell Disruptor, model W185, Branson Ultrasonics Corp, Danbury, Conn.). Tubes with 100 µl of TE alone were included as negative controls. 10 µl of the sonicated preparation were used for the PCR.

EXAMPLE 3

A. PCR Amplification of Eukarya-Specific 16S-like rDNA

PCR was performed using standard amplification conditions with the PCR Master Mix (above), Taq polymerase (1U "AmpliTaq", diluted in a volume of 10 µl; Perkin-Elmer Corp., Foster City, Calif.) and 20 pmoles of each primer in a total volume of 100 µl. Unless indicated otherwise, the Taq polymerase was added to the samples following the initial incubation at 95° C. for 3 min. Cycle parameters were typically 30s at 94° C., 30s at 50° C., and 30s at 72° C. for 30 cycles, followed by a 7 min. extension at 72° C. The PCR primers used are summarized in Table 1, below.

The amplification was carried out using Eukarya-specific primer 1FPL (SEQ ID NO:3) and universal primer 1520RPL (SEQ ID NO:4). After a "hot-start" and initial denaturation at 95° C. for 3 min, 40 cycles were conducted, each consisting of 94° C. for 1 min, 55° C. for 1 min, and 72° C. for 2 min.

PCR products were analyzed by electrophoresis in 1.2% agarose gels and visualized after ethidium bromide staining. Clinical sample handling, sonication, PCR set-up, and PCR product analysis were conducted in separate locations to minimize the potential for contamination.

Figure 1:
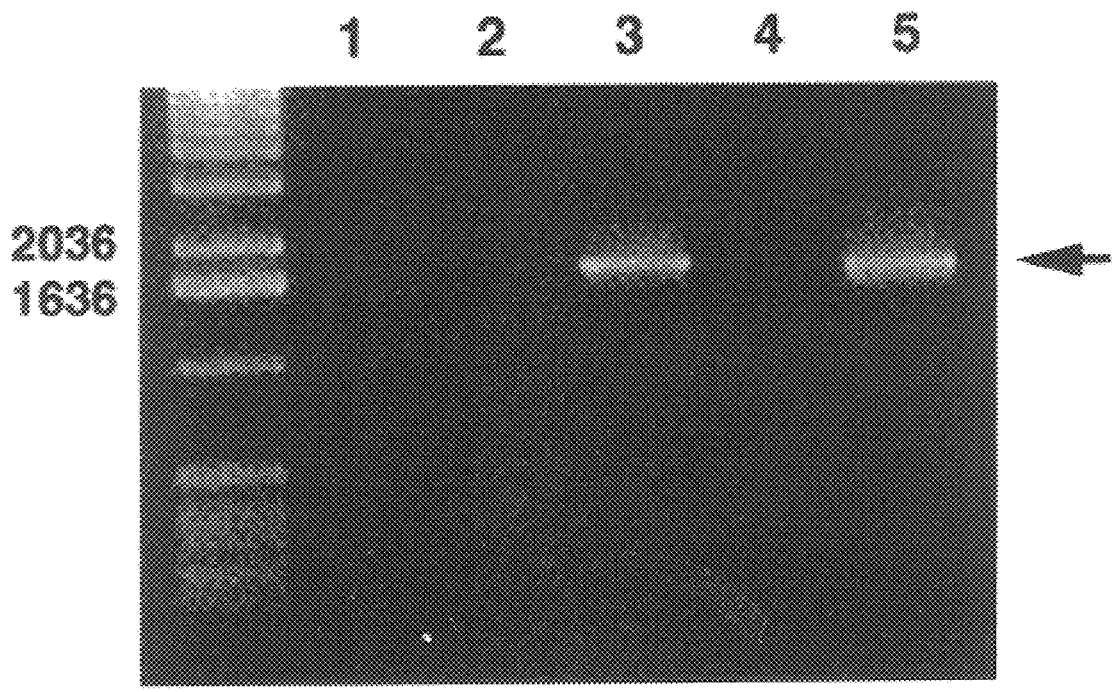
FIG. 1 is a scanned image of polymerase chain reaction (PCR) amplification products generated with Eukarya-specific primers 1FPL (SEQ ID NO:3) and 152ORPL (SEQ ID NO:4) from control and experimental samples containing various species of Apicomplexa.

The results are shown in FIG. 1. Lanes are as follows: lane 1, PCR reagents alone; lane 2, stool fraction from asymptomatic control; lane 3, stool fraction from patient with Cyclospora; lane 4, a member of the domain Bacteria, *Bordetella bronchiseptica;* and lane 5, *Cryptosporidium parvum.* Chromosomal DNA from *Cryptosporidium parvum* served as a positive control for reactions using this primer pair (FIG. 1, lane 5); a product size of 1766 bp is predicted by the *C. parvum* 16S-like rDNA sequence (Johnson, et al., 1990; Cai, et al., 1992). The product in lane 3 from the Cyclospora (arrow) was cloned and sequenced as described below. One kb DNA ladder (Life Technologies, Gaithersburg, Md.) is shown at far left.

As can be appreciated from the figure, this reaction generated a single DNA product of approximately 1700–1800 bp in size (FIG. 1, lane 3). Reactions with PCR reagents alone, or with a gradient fraction of a sonicated stool from an asymptomatic person at the same Nepalese clinic prepared under identical conditions, or with Bordetella bronchiseptica DNA were all negative (FIG. 1, lanes 1,2,4, respectively).

The PCR product generated by primers 1FPL (SEQ ID NO:3) and 1520RPL (SEQ ID NO:4) from the Cyclospora-containing sample above, as well as similar PCR products generated from 16S-like rRNA sequences from *Eimeria nieschulzi* (1797 bp), *E. tenella* (1756 bp), and *E. mitis* (1749 bp), were cloned in "pBluescript" (Stratagene, La Jolla, Calif.). The inserts were sequenced with a cycle-sequencing protocol using conserved rDNA priming sites, and an automated DNA sequencer (Applied Biosystems 373A, Foster City, Calif.) following the manufacturer's instructions. The Cyclospora sequence is provided herein as SEQ ID NO:1.

Multiple clones of each product were sequenced in order to assess possible heterogeneity among different rRNA gene copies.

B. PCR Detection of Cyclospora in Berries

Template DNA from berries was typically prepared for PCR using one of the protocols described below.

TABLE 1

| Primer | Sequence (5'→3') | SEQ ID NO: | Position |
|---|---|---|---|
| 1FPL | GCGGATCCGCGGCCGCTGGTTGATCCTGCCAGT | 3 | 4–20[a] |
| 1520RPL | GCGGATCCGCGGCCGCYGCAGGTTCACCTAC | 4 | 1860–1845[a] |
| CYCF1E | GGAATTCCTACCCAATGAAAACAGTTT | 5 | 418–436[b] |
| CYCR2B | CGGGATCCAGGAGAAGCCAAGGTAGG | 6 | 1053–1035[b] |
| CYCF3E | GGAATTCCTTCCGCGCTTCGCTGCGT | 7 | 685–704[b] |
| CRCR4B | CGGGATCCCGTCTTCAAACCCCCTACTG | 8 | 978–959[b] |

[a]underlined bases in primer sequence correspond to indicated positions in *Dictyostelium discoideum* 17S rRNA (Medlin, et al., 1988).

1. Target Preparation.

To the suspension of the pellet from Example 1.B.1. was added 0.3 g of glass beads. The resulting suspension was agitated with a vortex mixer set at full speed, three times for 5 minutes each (with chilling on ice between sessions). The sample was then centrifuged at 10,000 RPM for approximately 5 minutes and the supernatant used for PCR analysis.

2. Target Preparation.

In a modified approach, 20 µL Instagene DNA Purification Mix (Bio-Rad) was added to the final pellet from Example 1.B.2. and the mixture was vortexed to resuspend the pellet. Washed sediment was then subjected to 6 cycles of freeze-thawing in a liquid nitrogen bath for 2 minutes followed by water bath at 98° C. for 2 minutes. The mixture was vortexed thoroughly then centrifuged at 14,000 RPM for 3 minutes. The supernatant was then retained for PCR analysis.

3. PCR Analysis.

PCR analysis of berries was performed using two portions, 20 µL pure lysate and 20 µL of a 1:10 dilution of lysate, of template in separate PCR reactions. The 1:10 dilution was prepared by placing 2 µL of lysate in 10 µL 1× PCR Buffer. A suspension of 50 mg/ml instant nonfat dry milk in sterile distilled water was prepared. 2 µL of the milk suspension was added to each 20 µL portion of berry lysate and the entire 22 µL volume was used as the template for PCR.

PCR analysis consisted of two rounds of PCR using nested primers. Amplified product from the first round PCR was used as template for the second round PCR. Primers were prepared as 4 uM working solutions. First round amplification was carried out using primer CYCF1E (SEQ ID NO:5) and primer CYCR2B (SEQ ID NO:6). Second round amplification was carried out using primer CYCF3E (SEQ ID NO:7) and CYCR4B (SEQ ID NO:8).

The first round of amplification was carried out using the following reagents: 49.7 µL deionized water, 8.0 µL 10× PCR Buffer I (50 mM KCl, 10 mM Tris-HCl pH 8.3, 1.5 mM $MgCl_2$, 0.001 gelatin), 8.0 µL dNTP mix, 2.0 µL $MgCl_2$, 5 µL of each primer, 0.3 µL "Amplitaq", 22.0 µL template DNA, under standard amplification conditions. Cycle parameters were 5 minutes at 95° C.; 30 seconds at 94° C., 30 seconds at 53° C., 90 seconds at 72° C. for 35 cycles; followed by a 10 minute extension at 72° C. The reaction mixtures were held at 8° C. until second round amplification. In addition to the sample composites, a negative control (no template) and a positive control (Cyclospora DNA) were also evaluated.

Second round amplification was carried out as described for first round amplification above, with the following exceptions. Primers CYCF3E and CYCR4B (5 µL each) were used, and 5 µL of amplified product from the first round PCR was used as template for the second round PCR. For the positive control, the amplified product from the first round was diluted 1:10 and 5 µL of that dilution was used as template for the second round PCR. Cycle parameters were 5 minutes at 95° C.; 30 seconds at 94° C., 30 seconds at 60° C., 90 seconds at 72° C. for 35 cycles; followed by a 10 minute extension at 72° C. The resultant reaction mixtures were held at 8° C.

PCR products were analyzed by electrophoresis in 2% agarose gels and visualized by ethidium bromide staining. 10 µL of PCR product was mixed with 2 µL loading buffer and the entire volume was then loaded into the gel. The gel was electrophoresed in TBE at 100 volts for 1.5 hours.

The predicted size of the amplified product after the second round amplification was 294 bp.

EXAMPLE 4

Phylogenetic Analyses

The 1747 bp Cyclospora sequence (SEQ ID NO:1) and nearly complete 16S-like rDNA sequences from three Eimeria spp. were aligned with a collection of 16S-like rRNA sequences that included many available apicomplexan sequences as well as representative plant, fungal, and animal sequences deposited with the Ribosomal Database Project (Maidak, et al., 1994), GenBank and EMBL. Nucleotide positions judged to be aligned unambiguously (approximately 1500) were used in a parsimony analysis using the computer program PAUP3.2 (Swofford, 1991).

Phylogenetic trees were constructed by three different algorithms: 1) maximum parsimony using the software package PAUP 3.2 (Swofford, 1991) (FIG. 2); 2) the least squares method of DeSoete (DeSoete, et al., 1983); and 3) maximum-likelihood (FastDNAml; Olsen, et al., 1994). Bootstrap values for the dendrogram generated by PAUP (FIG. 2) were obtained from 100 resamplings (100 replications in which the branch and bound algorithm was used to find the best tree among all replicates). The percentage of 100 bootstrap resamplings that corroborate topological elements is given at branch nodes. G. max (soybean), O. granulifera, D. grandis, and S. cerevisiae serve as outgroups for the apicomplexans. Horizontal line lengths are proportional to the number of steps assigned to topological elements in the tree. Similarities were calculated using the correction of Jukes and Cantor (1969) as modified by Olsen (Weisburg, et al., 1989) for the positions considered in the phylogenetic analysis, or with all positions in the clade composed of Eimeria and Cyclospora sequences. The results are shown in FIG. 2 and Table 2, below.

TABLE 2

Distance Matrix of Small Subunit rDNA
Sequence Phylogenetic Dissimilarities (%)

| Organism | Cyc | Em | Et | En | Tg | Sm | Bm | Ta | Cp | Og | Gm | Dg |
|---|---|---|---|---|---|---|---|---|---|---|---|---|
| Cyclospora | | 4.4 | 4.0 | 4.6 | | | | | | | | |
| Eimeria mitis | 2.2 | | 4.0 | 5.5 | | | | | | | | |
| Eimeria tenella | 1.5 | 1.1 | | 5.2 | | | | | | | | |
| Eimeria nieschulzi | 2.8 | 3.1 | 2.2 | | | | | | | | | |
| Toxoplasma gondii | 8.2 | 8.4 | 7.7 | 8.4 | | | | | | | | |
| Sarcocystis muris | 8.0 | 8.5 | 7.6 | 8.0 | 1.8 | | | | | | | |
| Babesia microti | 11.9 | 12.2 | 11.5 | 11.8 | 9.2 | 9.0 | | | | | | |
| Theileria annulata | 11.6 | 11.9 | 11.2 | 11.3 | 8.6 | 8.6 | 5.2 | | | | | |
| Cryptosporidium parvum | 11.9 | 12.0 | 11.5 | 11.8 | 8.6 | 8.0 | 9.0 | 8.9 | | | | |
| Oxytricha granulifera | 15.5 | 16.6 | 16.1 | 15.8 | 13.1 | 13.0 | 13.8 | 13.1 | 11.5 | | | |
| Glycine max | 17.9 | 18.3 | 17.3 | 17.5 | 15.6 | 15.1 | 16.3 | 15.9 | 15.0 | 15.8 | | |

TABLE 2-continued

Distance Matrix of Small Subunit rDNA
Sequence Phylogenetic Dissimilarities (%)

| Organism | Cyc | Em | Et | En | Tg | Sm | Bm | Ta | Cp | Og | Gm | Dg |
|---|---|---|---|---|---|---|---|---|---|---|---|---|
| Diaphanoeca grandis | 15.4 | 15.8 | 15.2 | 15.0 | 13.8 | 13.4 | 14.8 | 14.2 | 12.0 | 13.0 | 12.6 | |
| Saccharomyces cerevisiae | 16.8 | 17.3 | 16.5 | 16.8 | 15.8 | 15.5 | 16.9 | 15.3 | 14.1 | 14.4 | 14.0 | 9.1 |

Abbreviations in column headings are same as organisms in left column. Values below diagonal represent phylogenetic dissimilarity scores calculated only with masked positions (1501). Values above diagonal (bold) were calculated using all available (unmasked) small subunit rDNA positions. Only Eimeria sequences could be aligned with the Cyclospora sequence using this more complete set of sequence positions.

Phylogenetic analysis of the 1747 bp Cyclospora sequence suggested that Cyclospora is most closely-related to the Eimeria genus (FIG. 2, Table 2).

Cyclospora and Eimeria formed a monophyletic group in 100% of bootstrap resamplings, representing a recently divergent clade within the apicomplexans. In 85% of these resamplings Cyclospora shared a more recent common ancestor with E. mitis and E. tenella—which are both found predominantly in chickens, than did the three with E. nieschulzi—which is found predominantly in rats. When the same nucleotide positions were considered using maximum likelihood and distance algorithms (DeSoete, 1983; Olsen, et al., 1994), trees of identical topology were generated. In support of the phylogenetic tree in FIG. 2, the distance values show Cyclospora cayetanensis to be 98.5% similar to E. tenella (based on the sites used in the parsimony analysis; but 96% similar when all available sites were considered), while E. nieschulzi is 97.8% similar to E. tenella (Table 2).

EXAMPLE 5

Nested PCR Amplification of Range-Restricted Cyclospora 16S-like rDNA

Nested PCR was performed to positively identify the presence of Cyclospora DNA in fecal samples. Unless indicated otherwise, each PCR was performed as described above using standard amplification conditions with the PCR Master Mix (above), 1U "AmpliTaq" Taq polymerase, and 20 pmoles of each primer indicated in a total volume of 100 µl.

An initial 30 cycles of PCR were run as described above with an annealing temperature of 50° C. and an outer primer pair consisting of primers CYCF1E (SEQ ID NO:5) and CYCR2B (SEQ ID NO:6). A second set of reactions was run for 30 cycles, using 5 µl of the initial reaction material as target, an annealing temperature of 60° C., and an inner primer pair consisting of primers CYCF3E (SEQ ID NO:7) and CYCR4B (SEQ ID NO:8). Cycle parameters for the second set of reactions were typically 30s at 94° C., 30s at 60° C., and 30s at 72° C. for 30 cycles, followed by a 7 min. extension at 72° C.

Figure 3:
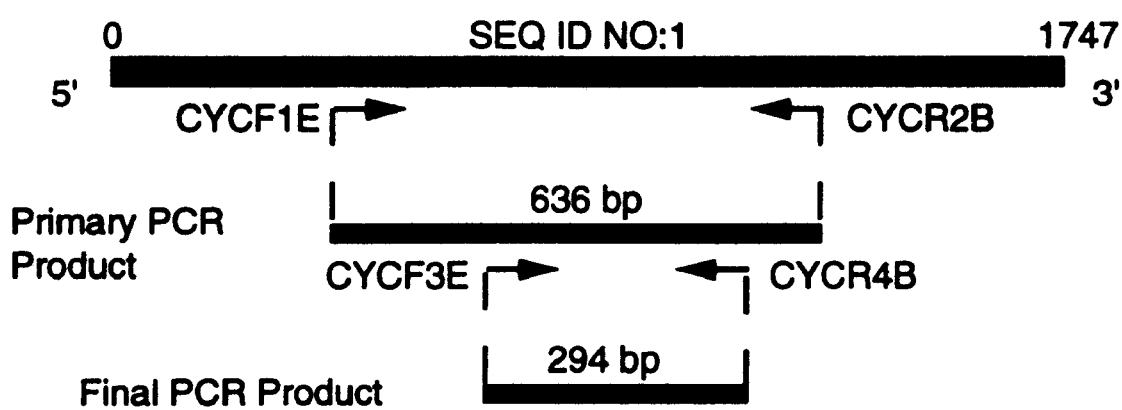
FIG. 3 is a schematic representation of the 1747 bp 16S-like *Cyclospora cayetanensis* rRNA sequence (SEQ ID NO:1), PCR products amplified in an exemplary nested PCR protocol, and relative locations of the primers used in the nested amplification procedure.

The relative positions of the primers used in the nested PCR reactions are shown in FIG. 3. The product sizes illustrated in FIG. 3 do not include the 5' portions of the primers which contain restriction sites to facilitate subsequent cloning.

PCR products generated as described above were analyzed by electrophoresis in 1.2% agarose gels as described above. Similar precautions to those described above were observed with respect to clinical sample handling, sonication, PCR set-up, and PCR product analysis.

Figure 4A:
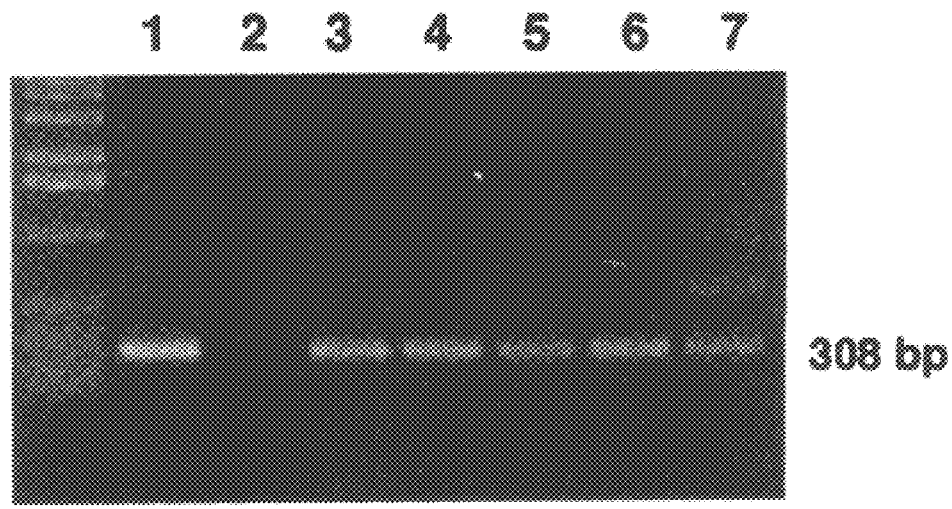
FIGS. 4A and 4B are scanned images of PCR products generated with range-restricted Cyclospora primers.
Figure 4B:

The results are shown in FIGS. 4A and 4B. A 1 kb DNA ladder (Life Technologies, Gaithersburg, Md.) is shown at far left of FIG. 4A and far right of FIG. 4B. Lanes are as follows. In FIG. 4A, lane 1, Cyclospora oocyst from index case; lane 2, PCR reagents alone; lanes 3–6, independent clinical samples containing Cyclospora oocysts; lane 7, Eimeria bovis chromosomal DNA. In FIG. 4B, lane 8, Cyclospora oocyst from index case; lane 9, asymptomatic human without visible oocysts; lane 10, human cryptosporidiosis stool sample; lane 11, Toxoplasma gondii chromosomal DNA; lane 12, Babesia microti chromosomal DNA; lane 13, Cryptosporidium parvum chromosomal DNA; and lane 14, bovine Neospora chromosomal DNA.

As can be appreciated from the Figure, products of the expected size (a 308-bp product, which includes the restriction site adapters on the primers, is expected from Cyclospora and Eimeria) were amplified from E. bovis, E. nieschulzi, and E. veriformis chromosomal DNA. The results indicate that the 308 bp fragments were amplified from as few as ~200–300 copies of cloned Cyclospora 16S-like rDNA (as few as ~10–50 purified oocysts). This assay also successfully discriminated these targets from human Toxoplasma, Babesia microti, Neospora, and Cryptosporidium parvum (FIG. 4B). In addition, stool samples prepared by sucrose flotation methods from two asymptomatic humans and from two humans with intestinal cryptosporidiosis were negative with this nested PCR assay, despite the ability to amplify human beta-globin gene sequences in these samples (indicating lack of PCR inhibitors).

In total, sonicates of sucrose flotation-purified Cyclospora samples from eight patients all yielded PCR products of the expected size with the nested range-restricted Cyclospora primers. These eight products, as well as product from the original isolate, NPL-233, were sequenced directly.

PCR products generated in the nested range-restricted procedure (described in Example 6, below) were partially purified with Centricon-100 concentrators (Amicon Corp, Beverly, Mass.) and both strands sequenced with a similar protocol using primers CYCF3E and CYCR4B. All fifteen 254 bp sequences (internal to the primers) were identical to the corresponding region of the original 1747 bp Cyclospora 16S-like rDNA sequence. Within this region (Cyclospora 16S-like rDNA sequence positions 705–958), the Cyclospora sequence differed at 6–10 nucleotide positions with the three Eimeria sequences. These results provide strong support for multiple Cyclospora isolates sharing the same 16S-like (18S) rDNA sequence.

In the region amplified by the outer primer pair (SEQ ID NO:5, SEQ ID NO:6), seven sequences assayed (598 nucleotides internal to the primers) were also identical to the corresponding region of the original 1747 bp Cyclospora 16S-like rDNA sequence (SEQ ID NO:1), with the exception of the nucleotides at positions 666 and 675. In some isolates, position 666 was a "T", while in others it was a "C". Similarly, position 675 was a "C" in some isolates and a "T" in others. This degeneracy is embodied in the Cyclospora 18S rRNA consensus sequence, presented herein as SEQ ID NO:2 (core sequence).

EXAMPLE 6

Cyclosora-Specific Sequences in the 16S-like rDNA

Sequence analyses and alignments of sequences of PCR products generated as described above revealed several regions of the Cyclospora 18S rRNA sequence (SEQ ID NO:1) which are less conserved with the three Eimeria sequences described above than other regions. These regions include those corresponding approximately to the following ranges in SEQ ID NO:1: (i) nt 150 to nt 210; (ii) nt 240 to nt 280; nt 620 to nt 725; nt 1307 to nt 1377; nt 1467 to nt 1518; and nt 1588 to 1700. Accordingly, these regions may be used to design PCR, OLA and/or LCR primers, as well as hybridization probes, which are selective for Cyclospora over Eimeria. The design and synthesis of PCR, OLA and/or LCR primers, as well as hybridization probes, is well known in the art.

Additionally, specific nucleotide positions were identified as being different in all three of the most-closely-related Eimeria spp. relative to the Cyclospora sequence presented as SEQ ID NO:1. These positions, termed "discriminating or discrimination positions" include the following (numbering refers to positions in SEQ ID NO:1): 155, 178, 249, 258, 262, 328, 473, 495, 501, 507, 636, 660, 667, 698, 706, 831, 1473, 1579, 1654, 1659, 1664, 1674, 1675, 1684 and 1694.

PCR primers whose 3' ends correspond to one of the above positions may be used to selectively amplify Cyclospora sequences from a sample containing both Cyclospora and Eimeria sequences, since PCR amplification is highly-dependent on a match between the primer and target at the 3' end of the primer (e.g., Sharrocks, 1994).

While the invention has been described with reference to specific methods and embodiments, it is appreciated that various modifications and changes may be made without departing from the invention.

It is claimed:

1. A method of detecting the presence of Cyclospora in a sample, comprising, reacting said sample with one or more oligonucleotides having a sequence matching a sequence in SEQ ID NO:2 in a region which includes at least one discrimination position in SEQ ID NO:2 selected from the group consisting of positions at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694, said reacting being performed under conditions in which said one or more oligonucleotides anneal with Cyclospora DNA in said sample; and by said reacting, producing a DNA product whose formation depends on hybridization of said one or more oligonucleotides to Cyclospora DNA.

2. The method of claim 1, wherein said reacting includes performing a hybridization detection assay.

3. The method of claim 2, wherein said assay is performed on a substrate containing a plurality of different-sequence polynucleotide fragments.

4. The method of claim 3, wherein said different-sequence polynucleotide fragments include target sequences for a plurality of different human intestinal pathogens.

5. The method of claim 3, wherein the different-sequence polynucleotide fragments are arranged in a grid.

6. The method of claim 5, wherein the substrate is a chip.

7. The method of claim 2, wherein said assay is performed using a hybridization probe having sequence identical to a region of SEQ ID NO:2 selected from the group consisting of regions defined by nucleotide positions 150–210, 240–280, 620–725, 1467–1518, and 1588–1700, or fragment of such a region, said fragment being at least about 20 nucleotides in length.

8. The method of claim 1, wherein said reacting includes performing a polymerase chain reaction amplification.

9. The method of claim 8, wherein said polymerase chain reaction amplification is performed using a primer set in which at least one primer is designed such that the nucleotide at the 3' end of the at least one primer is one of the nucleotides at one of said discrimination positions.

10. The method of claim 1, wherein said reacting includes performing an oligonucleotide ligation assay.

11. The method of claim 10, wherein said assay is performed using a primer set consisting of an upstream primer and a downstream primer, where the 3'end of the upstream primer is one of the one of the nucleotides at one of said discrimination positions.

12. The method of claim 10, wherein said assay is performed using a primer set in which one of the primers has a sequence which (i) spans one of said discrimination positions, and (ii) fails to hybridize to its target if there are one or more mismatches between the one of the primers and its target.

13. A method of detecting the presence of Cyclospora in a sample containing DNA, comprising, amplifying the DNA by polymerase chain reaction (PCR) using a first primer set, consisting of a first primer and a second primer, where at least one of said primers includes at least one discrimination position selected from the group consisting of positions in SEQ ID NO:2 at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694, to generate a first set of amplification products, and identifying, in said first set of amplification products, the presence of Cyclospora-specific 18S rRNA amplification products, wherein the presence of such Cyclospora-specific 18S rRNA amplification products indicates the presence of Cyclospora in said sample.

14. The method of claim 13, wherein said first primer and said second primer are selected to generate amplification products containing a sequence identical to the region of SEQ ID NO:2 between about nucleotides 420 and 1050.

15. The method of claim 14, wherein said first primer has a sequence identical to the region of SEQ ID NO:2 between about positions 418 and 436, and said second primer has a sequence identical to the region of SEQ ID NO:2 between about positions 1035 and 1053.

16. The method of claim 15, wherein said first primer has the sequence provided as SEQ ID NO:5 and said second primer has the sequence provided as SEQ ID NO:6.

17. The method of claim 13, wherein said primer set is selected to generate amplification products containing a sequence identical to the region of SEQ ID NO:2 between about nucleotides 685 and 980.

18. The method of claim 17, wherein said first primer has a sequence identical to the region of SEQ ID NO:2 between about positions 685 and 704, and said second primer has a sequence identical to the region of SEQ ID NO:2 between about positions 959 and 978.

19. The method of claim 18, wherein said first primer has the sequence provided as SEQ ID NO:7 and said second primer has the sequence provided as SEQ ID NO:8.

20. The method of claim 13, wherein said Cyclospora is C. cayetanensis.

21. The method of claim 13, wherein the presence of Cyclospora-specific 18S rRNA amplification products is identified by analyzing the size distribution of the amplification products.

22. The method of claim 13, wherein said sample is obtained from a human subject.

23. The method of claim 22, where said sample is a stool sample.

24. The method of claim 13, wherein the presence of Cyclospora-specific 18S rRNA amplification products is identified by sequencing amplification products having a size expected from the relative locations of the first and second primers on SEQ ID NO:2.

25. The method of claim 13, wherein said sample is obtained from a fruit.

26. The method of claim 25, wherein said fruit is a berry.

27. The method of claim 13, wherein said sample is obtained from a vegetable.

28. The method of claim 13, wherein said sample is obtained from a water supply.

29. The method of claim 13, further comprising amplifying the first set of amplification products by polymerase chain reaction using a second primer set, consisting of a third primer and a fourth primer, where the third and fourth primers each have a sequence identical to a region of SEQ ID NO:2 amplified by the first primer set, to generate a second set of amplification products, and identifying, in said second set of amplification products, the presence of Cyclospora-specific 18S rRNA amplification products.

30. The method of claim 29, wherein said first primer set is selected to generate amplification products containing a sequence identical to the region of SEQ ID NO:2 between about nucleotides 420 and 1050, and said second primer set is selected to generate amplification products containing a sequence identical to the region of SEQ ID NO:2 between about nucleotides 685 and 980.

31. The method of claim 30, wherein said first primer set consists of first and second primers having sequences identical to the region of SEQ ID NO:2 between about positions 418 and 436, and between about positions 1035 and 1053, respectively, and said second primer set consists of third and fourth primers having sequences identical to the region of SEQ ID NO:2 between about positions 685 and 704, and between about positions 959 and 978, respectively.

32. The method of claim 31, wherein said first primer has the sequence provided as SEQ ID NO:5, said second primer has the sequence provided as SEQ ID NO:6, said third primer has the sequence provided as SEQ ID NO:7 and said fourth primer has the sequence provided as SEQ ID NO:8.

33. A method of detecting the presence of Cyclospora in a sample containing DNA, comprising,
  amplifying the DNA by polymerase chain reaction (PCR) using a first primer set, consisting of a first primer and a second primer, where the primers are designed to amplify a DNA fragment containing a sequence which includes one or more discrimination positions selected from the group consisting of positions in SEO ID NO:2 at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694, to generate a first set of amplification products, and
  identifying, in said first set of amplification products, the presence of Cyclospora-specific 18S rRNA amplification products,
  wherein the presence of such Cyclospora-specific 18S rRNA amplification products indicates the presence of Cyclospora in said sample.

34. A method of detecting a Cyclospora infection in a human subject, comprising
  obtaining a sample from said subject,
  isolating DNA-containing oocysts from said sample,
  amplifying the oocyst DNA by polymerase chain reaction (PCR) using a first primer set, consisting of a first primer and a second primer, where the primers are designed to amplify a DNA fragment containing a sequence which includes one or more discrimination positions-selected from the group consisting of positions in SEO ID NO:2 at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694, to generate a first set of amplification products, and
  identifying, in said first set of amplification products, the presence of Cyclospora-specific 18S rRNA amplification products,
  wherein the presence of such Cyclospora-specific 18S rRNA amplification is indicative of a Cyclospora infection in said human subject.

35. The method of claim 34, where said sample is a stool sample.

36. The method of claim 34, where said sample is a biopsy sample of the intestinal lining.

37. A set of PCR primers suitable for the detection of Cyclospora, comprising
  a first primer having a sequence identical to or fully complementary to a first region SEQ ID NO:2, and
  a second primer having a sequence identical to or fully complementary to a second region of SEQ ID NO:2,
  wherein the 3' nucleotide of at least one of said primers is selected from the group consisting of positions in SEQ ID NO:2 at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694.

38. A set of PCR primers suitable for the detection of Cyclospora, comprising
  a first primer having a sequence selected from the group consisting of SEQ ID NO:5 and SEQ ID NO:7, and
  a second primer having a sequence selected from the group consisting of SEQ ID NO:6 and SEQ ID NO:8.

39. A set of oligonucleotide ligation assay primers suitable for the detection of Cyclospora, comprising
  a first primer having a sequence identical to a first region of SEQ ID NO:2, and
  a second primer having a sequence identical to a second region of SEQ ID NO:2,
  wherein said first and second regions are adjacent one another on SEQ ID NO: 2, and the sequence of said first primer spans at least one discrimination position selected from the group consisting of positions in SEQ ID NO:2 at nucleotide numbers 155, 178, 249, 258, 262, 328, 473, 495, 501, 507, 636, 660, 667, 698, 706, 831, 1473, 1579, 1654, 1659, 1664, 1674, 1675, 1684 and 1694.

40. The set of claim 39, wherein said first region is upstream said second region, and the 3' nucleotide of the first primer is one of said nucleotides at one of said discrimination positions.

41. The method of claim 8, which further includes identifying the size distribution of amplification products obtained from said polymerase chain reaction amplification.

42. The method of claim 8, which further includes sequencing amplification products obtained from said polymerase chain reaction amplification.

43. The method of claim 8, which further includes performing a hybridization assay using amplification products obtained from said polymerase chain reaction amplification.

* * * * *